United States Patent
DeLisa et al.

(10) Patent No.: US 11,192,942 B2
(45) Date of Patent: Dec. 7, 2021

(54) TARGETED PROTEIN SILENCING USING CHIMERAS BETWEEN ANTIBODIES AND UBIQUITINATION ENZYMES

(71) Applicant: CORNELL UNIVERSITY, Ithaca, NY (US)

(72) Inventors: Matthew DeLisa, Ithaca, NY (US); Jeffrey Varner, Ithaca, NY (US); Alyse Portnoff, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/379,309

(22) Filed: Apr. 9, 2019

(65) Prior Publication Data

US 2019/0233507 A1   Aug. 1, 2019

Related U.S. Application Data

(63) Continuation of application No. 14/007,784, filed as application No. PCT/US2012/030847 on Mar. 28, 2012, now abandoned.

(60) Provisional application No. 61/468,435, filed on Mar. 28, 2011.

(51) Int. Cl.
| | |
|---|---|
| *C07K 16/18* | (2006.01) |
| *C07K 16/00* | (2006.01) |
| *C12N 9/00* | (2006.01) |
| *A61K 38/00* | (2006.01) |

(52) U.S. Cl.
CPC .............. *C07K 16/18* (2013.01); *C07K 16/00* (2013.01); *C12N 9/93* (2013.01); *C12Y 603/02019* (2013.01); *A61K 38/00* (2013.01); *C07K 2319/00* (2013.01); *C07K 2319/50* (2013.01); *C07K 2319/95* (2013.01)

(58) Field of Classification Search
CPC .... C07K 16/18; C07K 16/00; C07K 2319/00; C07K 2319/50; C07K 2319/95; C07K 2317/622; C07K 2317/54; C07K 2317/55; C07K 2317/569; C07K 2317/624; C07K 2317/31; C07K 16/40; C07K 16/08; C12Y 603/02019; C12N 9/93; A61K 38/00
See application file for complete search history.

(56) References Cited

U.S. PATENT DOCUMENTS

| | | | |
|---|---|---|---|
| 7,892,772 B2 | 2/2011 | Rohde et al. | |
| 2002/0177212 A1* | 11/2002 | Patterson | ........... C07K 14/4703 435/226 |
| 2004/0146964 A1 | 7/2004 | Maxwell et al. | |
| 2005/0181420 A1 | 8/2005 | Patterson et al. | |
| 2010/0015116 A1* | 1/2010 | Oyler | ...................... C12N 9/93 424/94.1 |
| 2013/0011920 A1 | 1/2013 | Zhou et al. | |
| 2013/0281324 A1* | 10/2013 | Gouliaev | ........... C12N 15/1068 506/26 |
| 2014/0057807 A1 | 2/2014 | Loew et al. | |
| 2014/0112922 A1 | 4/2014 | DeLisa et al. | |

OTHER PUBLICATIONS

Tremblay et al., Toxicon 56: 990-998 (Year: 2010).*
Ishigaki et al., "Dorfin-CHIP Chimeric Proteins Potently Ubiquitylate and Degrade Familial ALS-related Mutant SOD1 Proteins and Reduce their Cellular Toxicity," Neurobiology of Disease 25(2):331-341 (2006).
Nissim et al., "Methods for Targeting Biologicals to Specific Disease Sites," Trends in Molecular Medicine 10(6):269-274 (2004).
Hatakeyama et al., "Targeted Destruction of c-Myc by an Engineered Ubiquitin Ligase Suppresses Cell Transformation and Tumor Formation," Cancer Research 65(17):7874-7879 (2005).
Li et al., "Degradation of HER2 by Cbl-Based Chimeric Ubiquitin Ligases," Cancer Research 67(18):8716-8724 (2007).
Schneekloth et al., "Chemical Genetic Control of Protein Levels: Selective in Vivo Targeted Degradation," Journal of American Chemistry of Society 126(12):3748-3754 (2004).
Zhou, Pengbo, "Harnessing the Ubiquitination Machinery to Target the Degradation of Specific Cellular Proteins," Molecular Cell 751-775 (2000).
Wikipedia, "Ubiquitin" retrieved at http://en.wikipedia.org/wiki/Ubiquitination on Mar. 19, 2012.
Kipreos et al.,"The F-box Protein Family," Genome Biology 1(5):3002.1-3002.7 (2000).
Nelson et al., "A Novel Route for F-box Protein-mediated Ubiquitination Links CHIP to Glycoprotein Quality Control," The Journal of Biological Chemistry 281(29):20242-20251 (2006).
Zeng et al., "Classification, Expression Pattern, and E3 Ligase Activity Assay of Rice U-Box-Containing Proteins," Molecular Plant 1(5):800-815 (2008).
International Search Report and Written Opinion for PCT/US2012/030847, filed Mar. 28, 2012 (dated Oct. 24, 2012).
Melchionna & Cattaneo, "A Protein Silencing Switch by Ligand-Induced Proteasome-Targeting Intrabodies," J. Mol. Biol. 374:641-654 (2007).
Zhou P., "Targeted Protein Degradation," Curr. Opin. Chem. Biol. 9:51-55 (2005).
Jiang et al., "CHIP Is a U-Box-Dependent E3 Ubiquitin Ligase", J. Biol. Chem. 276(46):42938-42944 (2001).

(Continued)

*Primary Examiner* — Phuong Huynh
(74) *Attorney, Agent, or Firm* — Troutman Pepper Hamilton Sanders LLP (Rochester)

(57) ABSTRACT

The present invention relates to an isolated chimeric molecule comprising a degradation domain including a eukaryotic U-box motif and a targeting domain capable of immunospecifically directing the degradation domain to a substrate where the targeting domain is heterologous to the degradation domain. A linker couples the degradation domain to the targeting domain. Also disclosed are compositions as well as methods of treating a disease, substrate silencing, screening agents for therapeutic efficacy against a disease, and methods of screening for disease biomarkers.

14 Claims, 6 Drawing Sheets

Specification includes a Sequence Listing.

(56) References Cited

OTHER PUBLICATIONS

Stancovski et al., "Mechanistic Aspects of the Opposing Effects of Monoclonal Antibodies to the ERBB2 Receptor on Tumor Growth," PNAS 88:8691-8695 (1991).
Golay et al., "Mechanism of Action of Therapeutic Monoclonal Antibodies: Promises and Pitfalls of in Vitro and in Vivo Assays," Archives of Biochemistry and Biophysics 526:146-153 (2012).
Paul, W.E., "Fundamental Immunology" Third Edition, (textbook) pp. 292-295 (1993).
Hay et al., "Clinical Development Success Rates for Investigational Drugs," Nature Biotechnology 32(1):40-51 (2014).
Kumar et al., "Preclinical Models for Pediatric Solid Tumor Drug Discovery: Current Trends, Challenges and the Scopes for Improvement," Expert Opinion Drug Discov. 7(11):1093-1106 (2012).
Tol et al., "Chemotherapy, Bevacizumab, and Cetuximab in Metastatic Colorectal Cancer," N. Engl. J. Med. 5;360(6):563-72 (2009).
Doronina et al., "Enhanced Activity of Monomethylauristatin F Through Monoclonal Antibody Delivery: Effects of Linker Technology on Efficacy and Toxicity," Bioconjugate Chem. 17:114-124 (2006).
Portnoff et al., "Ubiquibodies, Synthetic E3 Ubiquitin Ligases Endowed with Unnatural Substrate Specificity for Targeted Protein Silencing," J. Biol. Chem. 289(11):7844-7855 (2014).
Xu et al., "Structure and Interactions of the Helical and U-Box Domains of CHIP, the C Terminus of HSP70 Interacting Protein," Biochemistry 45:4749-4759 (2006).
Ballinger et al., "Identification of CHIP, a Novel Tetratricopeptide Repeat-Containing Protein that Interacts with Heat Shock Proteins and Negatively Regulates Chaperone Functions," Molecular and Cellular Biology 19(6):4535-4545 (1999).
Rudikoff et al., "Single Amino Acid Substitution Altering Antigen-Binding Specificity," PNAS 79:1979-1983 (1982).
International Search Report and Written Opinion for International Patent Application Serial No. PCT/US2019/22783 (dated Aug. 22, 2019).
Ashida et al., "A Bacterial E3 Ubiquitin Ligase IpaH9.8 Targets NEMO/IKKy to Dampen the Host NF-kB-Mediated Inflammatory Response," Nat. Cell Biol. 12(1):66-9 (2010).
Ludwicki et al., "Broad-Sepctrum Proteome Editing with an Engineering Bacterial Ubiquitin Ligase Mimic," ACS Cent. Sci. 5(5)852-66 (2019).
Koegl et al., "A Novel Ubiquitination Factor, E4, is Involved in Multiubiquitination Chain Assembly," Cell 96:635-644 (1999).
Aravind and Koonin, "The U Box is a Modified Ring Finger: A Common Domain in Ubiquitination," Curr. Biol. 10:R132-R134 (2000).
Ohi et al., "Structural Insights into the U-Box, A Domain Associated with Multi-Ubiquitination" Nat. Struct. Biol. 10:250-255 (2003).
Qian et al., "Engineering a Ubiquitin Ligase Reveals Conformational Flexibility Required for Ubiquitin Transfer," J. Biol. Chem. 284(39): 26797-802 (2009).

* cited by examiner

TARGETED PROTEIN SILENCING USING CHIMERAS BETWEEN ANTIBODIES AND UBIQUITINATION ENZYMES

This application is a continuation of U.S. patent application Ser. No. 14/007,784, now abandoned, which is a national stage application under 35 U.S.C. § 371 of PCT Application No. PCT/US2012/030847, filed Mar. 28, 2012, which claims the priority benefit of U.S. Provisional Patent Application Ser. No. 61/468,435, filed Mar. 28, 2011, which is hereby incorporated by reference in its entirety.

This invention was made with government support under grants GM008500 and CA167100 awarded by the National Institutes of Health. The government has certain rights in the invention.

FIELD OF THE INVENTION

The present invention relates to targeted protein silencing using chimeras between antibodies and ubiquitination enzymes.

BACKGROUND OF THE INVENTION

Following discovery of the ubiquitin-proteasome system ("UPS") in the 1980's, researchers have exploited its capacity to function as a degradative regulator of protein profusion. The UPS ensures homeostatic concentrations of intracellular proteins via the proteasome, which recognizes and degrades ubiquitinated proteins. The process of ubiquitination involves a cascade of three enzymes, i.e., the ubiquitin activating enzyme ("E1"), the ubiquitin conjugating enzyme ("E2"), and the ubiquitin ligase ("E3"). In brief, target protein modification, through ubiquitination, occurs when ubiquitin is activated by E1, which then transfers the highly conserved ubiquitin molecules to an E2 intermediate. Finally, E3-mediated ligation permits the covalent attachment of ubiquitin to a substrate. Typically, ubiquitin-chain elongation occurs pursuant to the concerted action of E2 and E3, albeit through a process that is not completely understood. See Hochstrasser, M., "Lingering Mysteries of Ubiquitin-Chain Assembly." *Cell* 124(1): 27-34 (2006).

Ubiquitination imparts a conduit system for elucidating dynamic protein interactions by manipulating the cellular machinery, i.e., E1, E2, and E3. Previously, however, cellular characteristics could only be studied by employing, for example, genetic "knock-outs" or RNA interference ("RNAi") technology. Notwithstanding the benefits of such technology, systems that function at the genetic level fail to provide phenotypic insight into cellular processes and disease etiology. While modified ubiquitin E3 enzymes have been generated, these ligases are circumscribed insofar as they possess native substrate specificity.

The first successful in vivo redirection of a ubiquitin bound substrate—to the proteasome—was performed by engineering a multimeric E3 protein complex viz SCF (Skp1, Cullin, F box-containing proteins) in yeast. Zhou, et al., "Harnessing the Ubiquitination Machinery to Target the Degradation of Specific Cellular Proteins." *Mol Cell* 6(3): 751-756 (2000) ("Zhou 2000"). Zhou 2000 demonstrated that by generating chimeric proteins possessing a target protein binding partner, the F-box containing protein Cdc4p—which functions as a substrate recognition complex—could redirect the SCF complex to degrade the target protein. Furthermore, it was shown that the human homolog of Cdc4p, i.e., βTrCP, could be engineered to selectively degrade hypophosphorylated forms of target proteins. See Zhou (2000); Zhang et al. "Exploring the Functional Complexity of Cellular Proteins by Protein Knockout." *Proc Natl Acad Sci USA* 100(24): 14127-14132 (2003); and Zhou et al. "Targeted Protein Degradation." *Curr Opin Chem Biol* 9(1): 51-45 (2005) ("Zhou 2005").

Nevertheless, it was determined that the core SCF complex was encumbered by the overexpression of F-box chimeras, which therefore curtailed the ubiquitination of both native and novel substrates. See Zhou (2005). A simplified E3 chimera was created by utilizing a monomeric U-box ubiquitin ligase and fusing it to a known substrate, i.e., c-Myc, a proto-oncogene transcription factor. See Hatakeyama et al., "Targeted Destruction of c-Myc by an Engineered Ubiquitin Ligase Suppresses Cell Transformation and Tumor Formation." *Cancer Res* 65(17): 7874-7879 (2005). In each of these cases, however, pre-existing interactions with native proteins were required to facilitate degradation.

Moreover, it has been shown that the configuration of F-box proteins exclude the possibility of fusion with antibody single-chain fragments ("scFv") for use in targeted degradation. See Melchionna et al., "A Protein Silencing Switch by Ligand-induced Proteasome-targeting Intrabodies." *J. Mol. Biol.* 374, 641-654 (2007). Consequently, a facile approach for effective post-translational protein silencing remains an important consideration in the development of new strategies for elucidating novel molecular mechanisms, drug targets, therapeutic and prognostic determinations of disease, and research-based applications coterminous with the same.

The present invention is directed to overcoming the deficiencies in the art.

SUMMARY OF THE INVENTION

One aspect of the present invention relates to an isolated chimeric molecule comprising a degradation domain including a eukaryotic U-box motif and a targeting domain capable of immunospecifically directing the degradation domain to a substrate, where the targeting domain is heterologous to the degradation domain. A linker couples the degradation domain to the targeting domain.

A further aspect of the present invention relates to a composition comprising the chimeric molecule and a pharmaceutically-acceptable carrier. In some embodiments, a method of treating a disease involves administering the composition to a subject having a disease where the subject to whom the composition is administered has an increased expression level of a substrate compared to a subject not afflicted with the disease.

Another aspect of the present invention relates to a method for substrate silencing. The method involves selecting a substrate to be silenced and providing a chimeric molecule. The substrate and the chimeric molecule are contacted under conditions to permit the formation of a substrate-molecule complex, where the complex mediates the degradation of the substrate to be silenced.

The present invention also relates to screening agents for therapeutic efficacy against a disease. This method involves providing a biomolecule whose presence is mediated by a disease state. A test agent composed of (i) a degradation domain including a eukaryotic U-box motif, (ii) a targeting domain capable of immunospecifically directing the degradation domain to the biomolecule, where the targeting domain is heterologous to the degradation domain, and (iii) a linker coupling the degradation domain to the targeting domain are provided. The biomolecule and the test agent are contacted under conditions effective for the test agent to facilitate degradation of the biomolecule. The level of the biomolecule, as a result of the contacting, is determined and the test agent which, based on the determining, decreases the level of the biomolecule is identified as being a candidate for therapeutic efficacy against the disease.

Another aspect of the present invention relates to screening for disease biomarkers. This method involves providing a sample of diseased cells expressing one or more ligands. A plurality of chimeric molecules composed of (i) a degradation domain including a eukaryotic U-box motif, (ii) a targeting domain capable of immunospecifically directing the degradation domain to the one or more ligands, where the targeting domain is heterologous to the degradation domain, and (iii) a linker coupling the degradation domain to the targeting domain. The sample and the plurality of chimeric molecules are contacted under conditions effective for the diseased cells to fail to proliferate in the absence of the chimeric molecule. The chimeric molecules which permit the diseased cells to proliferate are determined, and the ligands which bind to the chimeric molecules determined to permit diseased cells to proliferate, are identified as biomarkers.

The present invention thus relates to chimeric molecules, compositions, treatments, pharmaceutical compositions, protein silencing techniques, the elucidation of therapeutic agents, and target screening technologies based on a novel class of chimeric molecules. Such chimeras, termed "ubiquibodies" herein, import the ligase function of an E3 ubiquitin enzyme to generate a molecule possessing target specificity. Such engineered chimeras facilitate the redirection and proteolytic degradation of specific substrate targets, which may not otherwise be bound for the proteasome.

In this respect, the targeted elimination of such specific substrates, e.g., intracellular proteins, ascribes a broad range of scientific and clinical indications to the chimeric molecules, compositions, treatments, pharmaceutical compositions, protein silencing techniques, elucidation of therapeutic agents, and screening technologies provided herein. The present invention therefore imparts a variety of valuable tools for employing and developing specific prognostic and therapeutic applications based on the proteolytic degradation of aberrantly expressed genes via ubiquitination.

In addition to exploiting the cellular ubiquitin-proteasome machinery by redirecting ubiquitin ligases, e.g., E3 ligases, the present invention provides techniques which obviate the endogenous interactions of targeted proteins. See Hatakeyama (2005); Qian et al., "Engineering a Ubiquitin Ligase Reveals Conformational Flexibility Required for Ubiquitin Transfer." *J Biol Chem* 284(39): 26797-802 (2009), which are hereby incorporated by reference in their entirety. In this way, the concerted redirection of a degradation domain E3 ligase from, e.g., CHIP, does not require protein/domain fusion with naturally occurring, native protein binding partners, to interact with a target substrate. Thus, the present invention expounds upon the conscribed degradation of proteins for which a naturally occurring ligand exists, has been identified, and is required, by employing intrabody-chimeras or "ubiquibodies" for the exploitation of ubiquitin-mediated proteolysis of targeted substrates.

While technologies such as gene targeting and RNAi are capable of abrogating protein expression, ubiquibodies function at the post-translational level to increase target protein turnover. Hence, ubiquibodies can be employed for analyzing post-translational events, e.g., phosphorylation, which could not otherwise be elucidated by simply blocking protein biosynthesis. In addition, insofar as ubiquibody synthesis can be constitutive or inducible, the level of inactivation can be manipulated, thereby allowing for controlled phenotypic assays. Moreover, ubiquibodies are more stable than RNAi molecules, and possess few functional constraints, e.g., they can be monovalent or multivalent, which therefore imparts a system for multiplexed target silencing. See Jendreyko et al., "Intradiabodies, Bispecific, Tetravalent Antibodies for the Simultaneous Functional Knockout of Two Cell Surface Receptors." *J Biol Chem* 278(48): 47812-9 (2003), which is hereby incorporated by reference in its entirety.

The present invention thus provides for a simple and efficient tool for creating artificial E3 ligases that enable the dissection of diverse functional properties of cellular proteins in somatic cells, and evaluation of whether specific cellular proteins are valid targets for therapeutic intervention. The ablation of intracellular protein targets as an effective therapeutic strategy for certain human malignancies and neurodegenerative diseases are implicated in this regard. Furthermore, because these methods are general in nature and extremely simple to implement, they could be developed and/or used in virtually any laboratory.

BRIEF DESCRIPTION OF THE DRAWINGS

FIG. 1A is a schematic depiction of pET28a constructs used to express ubiquibodies ("uAb") in *E. coli*, which includes single chain Fv antibody fragment ("scFv"), GSGSG linker ("~"), human C-terminus of Hsc70-interacting protein ("CHIP") without the N-terminal TPR domain ("CHIPΔTPR"), a FLAG-tag ("F") and a 6×His-tag ("H6"). FIG. 1B is a western blot of the soluble fractions isolated from BL21(DE3) *E. coli* cells expressing wild-type human CHIP, inactivated CHIPH260Q, CHIPΔTPR, scFv13R4, scFv13R4-uAb, scFv13-uAb and scFvD10-uAb. An equivalent amount of total protein was loaded in each lane and expression was assayed using anti-FLAG-HRP. FIG. 1C is a graph showing ELISA results where a plate was coated with 1 μg β-gal per well and incubated with 160 ng of purified protein per well. Samples were performed in triplicate and error bars represent the standard deviation of the mean. FIG. 1D is a graph showing ELISA results using 1 μg HA-gpD incubated in the presence of 160 ng of purified protein, per well. Reactions were performed in triplicate and error bars represent the standard deviation of the mean.

FIG. 2A shows the ubiquitination of β-gal (116 kDa) as a function of time where the reactions were allowed to proceed for the allocated time, as shown, at 37° C. and then stopped by boiling in the presence of 2×SDS-PAGE loading dye. Samples were separated via 8% SDS-PAGE and immunoblotted with anti-β-gal. Increased molecular weight is indicative of the covalent attachment of ubiquitin (8.4 kDa). FIG. 2B shows the results from an in vitro ubiquitination assay with β-gal which was performed in the presence of control E3 ubiquitin ligases, as compared to the endogenous ubiquibody, i.e., scFv13R4-uAb. Ubiquitination reactions were allowed to proceed for 2 hours at 37° C. and were subsequently evaluated by immunoblotting with antibodies against ubiquitin and Lys48-linked ubiquitin ("K48").

FIG. 4A shows the ubiquitination of His-HA-gpD (14.2 kDa) as a function of time. Reactions were allowed to proceed for the allocated time, as shown, at 37° C. and then terminated by adding 2×SDS-PAGE loading dye and boiling. Samples were separated using 4-20% SDS-PAGE and immunoblotted using anti-HA antibodies. Increased molecular weight is indicative of the covalent attachment of ubiquitin (8.4 kDa). FIG. 4B shows results from ubiquitin assays using the control ubiquitin ligase, CHIPΔTPR, as compared to the endogenous ubiquibody, scFvD10-uAb. Ubiquitination of His-HA-gpD proceeded for 2 hours at 37° C. and results were evaluated by immunobloting with antibodies against ubiquitin and K48.

FIG. 6A represent results from an ELISA with 1 μg Hsp70 incubated in the presence of 160 ng of purified protein. Reactions were performed in triplicate and error bars represent the mean standard deviation. FIG. 6B shows the ubiquitination of Hsp70 (72 kDa) as a function of time. Reactions were allowed to proceed, as shown, for the allocated time at 37° C. and terminated by boiling in the presence of 2×SDS-PAGE loading dye. Samples were separated using 4-20% SDS-PAGE and immunoblotted using an anti-Hsp70 antibody. FIG. 6C shows the ubiquitination of Hsp70 in the presence of control E3 ubiquitin ligases. The control lane represents ubiquitination at time 0. The remaining reactions proceeded for 2 hours at 37° C. and were evaluated by immunobloting with antibodies directed against ubiquitin and K48.

DETAILED DESCRIPTION OF THE INVENTION

Figure 1:
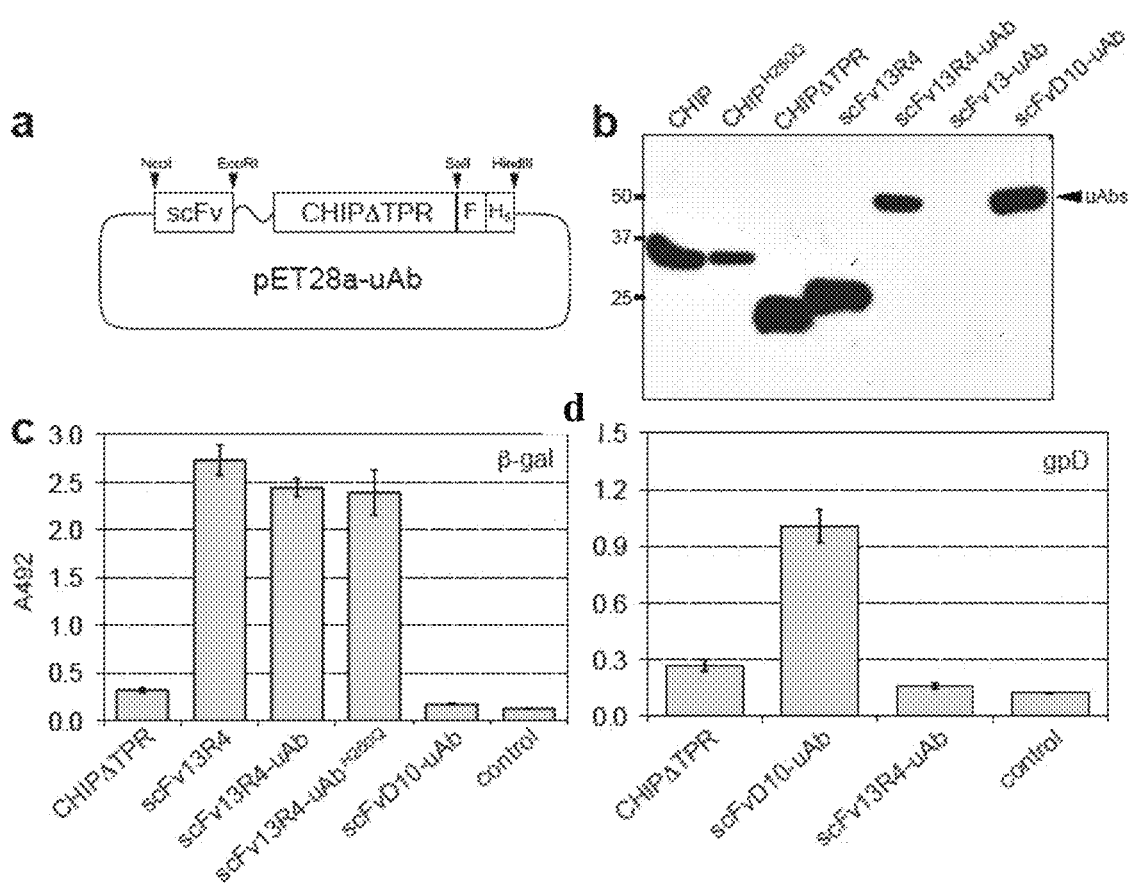
FIGS. 1A-D illustrate ubiquibody expression and binding.

It is to be appreciated that certain aspects, modes, embodiments, variations and features of the present invention are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this invention belongs.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y. (1989)); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); Immobilized Cells and Enzymes (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, New York (1987)); and *Meth. Enzymol.*, Vols. 154 and 155, Wu & Grossman, and Wu, Eds., respectively, which are hereby incorporated by reference in their entirety. Methods to detect and measure levels of polypeptide gene expression products, i.e., gene translation level, are well-known in the art and include the use polypeptide detection methods such as antibody detection and quantification techniques. See also, Strachan & Read, *Human Molecular Genetics*, Second Edition. (John Wiley and Sons, Inc., New York (1999), which is hereby incorporated by reference in its entirety.

As used herein, the term "amino acid" includes naturally-occurring amino acids, L-amino acids, D-amino acids, and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, e.g., an α-carbon that is bound to a hydrogen, a carboxyl group, an amino group, and an R group, e.g., homoserine, norleucine, methionine sulfoxide, methionine methyl sulfonium. Such analogs have modified R-groups, e.g., norleucine, or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission.

As used herein the term "antibody" refers to an immunoglobulin and any antigen-binding portion of an immunoglobulin, e.g., IgG, IgD, IgA, IgM and IgE, or a polypeptide that contains an antigen binding site, which specifically or "immunospecifically binds" to, or "immunoreacts with", an immunogen, antigen, substrate, and the like. Antibodies can comprise at least one heavy (H) chain and at least one light (L) chain inter-connected by at least one disulfide bond. The term "$V_H$" refers to a heavy chain variable region of an antibody. The term "$V_L$" refers to a light chain variable region of an antibody. In some embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells.

Antibody-related molecules, domains, fragments, portions, etc., useful as targeting domains of the invention include, e.g., but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Examples include: (i) a Fab fragment, a monovalent fragment consisting of the $V_L$, $V_H$, $C_L$ and $CH_1$ domains; (ii) a F(ab')$_2$ fragment, a bivalent fragment comprising two Fab fragments linked by a disulfide bridge at the hinge region; (iii) a Fd fragment consisting of the $V_H$ and $CH_1$ domains; (iv) a Fv fragment consisting of the $V_L$ and $V_H$ domains of a single arm of an antibody, (v) a dAb fragment (Ward et al., Nature 341:544-546, (1989)), which consists of a $V_H$ domain; and (vi) an isolated complementary determining region (CDR). As such "antibody fragments" can comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments. Single-chain antibody molecules may comprise a polymer with a number of individual molecules, for example, dimer, trimer or other polymers.

As used herein, the terms "biomarker" or "biomolecule" or "molecule" refer to a polypeptide (of a particular expression level) which is differentially present in a sample taken from patients having a disease as compared to a comparable sample taken from a control subject or a population of control subjects.

As used herein, the term "chimeric molecule" refers to a molecule possessing a degradation domain and a targeting region, as defined herein. The degradation domain and targeting region may be attached in manner known in the art. For example, they may be linked via linker molecule as defined herein, fused, covalently attached, non-covalently attached, etc. Moreover, the degradation domain and a targeting region may not be directly attached and/or the attachment may be transient, e.g., if a linker is used, the linker may be cleavable or non-cleavable.

As used herein, the terms "degradation domain" or "degradation region" refer to a portion of a chimeric molecule that is capable of facilitating the ubiquitination of a substrate. The degradation domain may have a second "binding" region for interaction with a native binding protein. The binding region can be modified as to possess one or more mutations, substitutions, deletions, or may be deleted entirely.

As used herein, the terms "effective amount" or "therapeutically effective amount" of a chimeric molecule or composition is a quantity sufficient to achieve a desired therapeutic and/or prophylactic effect, for example, an amount which results in the prevention of or a decrease in the symptoms associated with a disease that is being treated. The amount of compound administered to the subject will depend on the type and severity of the disease and on the characteristics of the individual, such as general health, age, sex, body weight and tolerance to drugs. It will also depend on the degree, severity or stage of disease. The skilled artisan will be able to determine appropriate dosages depending on these and other factors.

The term "enzyme linked immunosorbent assay" (ELISA) as used herein refers to an antibody-based assay in which detection of the antigen of interest is accomplished via an enzymatic reaction producing a detectable signal. An ELISA can be run as a competitive or non-competitive format. ELISA also includes a 2-site or "sandwich" assay in which two antibodies to the antigen are used, one antibody to capture the antigen and one labeled with an enzyme or other detectable label to detect captured antibody-antigen complex. In a typical 2-site ELISA, the antigen has at least one epitope to which unlabeled antibody and an enzyme-linked antibody can bind with high affinity. An antigen can thus be affinity captured and detected using an enzyme-linked antibody. Typical enzymes of choice include alkaline phosphatase or horseradish peroxidase, both of which generate a detectable product when contacted by appropriate substrates.

As used herein, the term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Typically, an epitope will be a determinant region form a substrate, which can be recognized by one or more target domains.

To screen for targeting domains or substrates which possess an epitope, a routine cross-blocking assay such as that described in Antibodies, A Laboratory Manual, Cold Spring Harbor Laboratory, Ed Harlow and David Lane (1988), which is hereby incorporated by reference in its entirety, can be performed. This assay can be used to determine if a target domain binds the same site or epitope of a substrate as a different targeting domain, antibody, antibody fragment and the like. Alternatively, or additionally, epitope mapping can be performed by methods known in the art. For example, the antibody sequence can be mutagenized such as by alanine scanning, to identify contact residues. In a different method, peptides corresponding to different regions of substrate can be used in competition assays with a test target domain or with a test antibody and a target domain or an antibody with a characterized epitope.

As used herein, the term "hypervariable region" refers to the amino acid residues of an antibody which are responsible for antigen-binding. The hypervariable region generally comprises amino acid residues from a "complementarity determining region" or "CDR", e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., Sequences of Proteins of Immunological Interest, 5th Ed. Public Health Service, National Institutes of Health, Bethesda, Md. (1991), which is hereby incorporated by reference in its entirety, and/or those residues from a "hypervariable loop" (e.g., residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)), which is hereby incorporated by reference in its entirety.

As used herein, the terms "isolated" or "purified" polypeptide, peptide, molecule, or chimeric molecule, is substantially free of cellular material or other contaminating polypeptides from the cell or tissue source from which the agent is derived, or substantially free from chemical precursors or other chemicals when chemically synthesized. For example, an chimeric molecule would be free of materials that would interfere with such a molecules intended function, diagnostic or therapeutic uses. Such interfering materials may include proteins or fragments other than the materials encompassed by the chimeric molecule, enzymes, hormones and other proteinaceous and nonproteinaceous solutes.

As used herein, the terms "ligand" or "substrate" refer to substance that are able to bind to and form transient or stable complexes with a protein, molecule, chimeric molecule, ligand (dimer), substrate (dimer), a second substrate, a second ligand, target domain, regions, portions, and fragments thereof, ubiquitin or U-box motif regions, domains, or portions thereof, biomolecules, biomarkers, and the like, to serve a biological purpose, for example a substrate which interacts with an enzyme in the process of an enzymatic reaction. Ligands also include signal triggering molecules which bind to sites on a target protein, by intermolecular forces such as ionic bonds, hydrogen bonds and Van der Waals forces. In some embodiments, substrates bind ligands and/or ligands bind substrates.

As used herein, the terms "modification(s)" or "amino acid modification" of a polypeptide, protein, region, domain, or the like, refers to a change in the native sequence such as a deletion, addition or substation of a desired residue. Such modified polypeptides are prepared by introducing appropriate nucleotide changes into the antibody nucleic acid, or by peptide synthesis. Any combination of deletion, insertion, and substitution is made to obtain the antibody of interest, as long as the obtained antibody possesses the desired properties. The modification also includes the change of the pattern of glycosylation of the protein. A useful method for identification of preferred locations for mutagenesis is called "alanine scanning mutagenesis" as described by Cunningham and Wells in *Science,* 244:1081-1085 (1989), which is hereby incorporated by reference in its entirety. The mutated antibody is then screened for the desired activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Nevertheless, the monoclonal antibodies to be used in accordance with the present invention may be made by the hybridoma method first described by Kohler et al., *Nature* 256:495 (1975), which is hereby incorporated by reference in its entirety, or may be made by recombinant DNA methods. See, e.g., U.S. Pat. No. 4,816,567, which is hereby incorporated by reference in its entirety. The "monoclonal antibodies" may also be isolated from phage antibody libraries using the techniques described in Clackson et al., *Nature* 352:624-628 (1991) and Marks et al., *J. Mol. Biol.* 222:581-597 (1991), for example, which are hereby incorporated by reference in their entirety.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polyclonal antibody" means a preparation of antibodies derived from at least two (2) different antibody-producing cell lines. The use of this term includes preparations of at least two (2) antibodies that contain antibodies that specifically bind to different epitopes or regions of an antigen.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular cross-linking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

As used herein, the terms "reference level" or "control level" refer to an amount or concentration of biomarker (or biomolecule, ligand, substrate and the like) which may be of interest for comparative purposes. In some embodiments, a reference level may be the level of at least one biomarker expressed as an average of the level of at least one biomarker taken from a control population of healthy subjects or from a diseased population possessing aberrant expression of a protein or substrate. In another embodiment, the reference level may be the level of at least one biomarker in the same subject at an earlier time, i.e., before the present assay. In even another embodiment, the reference level may be the level of at least one biomarker in the subject prior to receiving a treatment regime.

As used herein, the term "sample" may include, but is not limited to, bodily tissue or a bodily fluid such as blood (or a fraction of blood such as plasma or serum), lymph, mucus, tears, saliva, sputum, urine, semen, stool, CSF, ascities fluid, or whole blood, and including biopsy samples of body tissue. A sample may also include an in vitro culture of microorganisms grown from a sample from a subject. A sample may be obtained from any subject, e.g., a subject/patient having or suspected to have a disease or condition characterized by a disease.

As used herein, the term "screening" means determining whether a chimeric molecule or composition has capabilities or characteristics of preventing or slowing down (lessening) the targeted pathologic condition stated herein, namely a disease or condition characterized by defects in specified disease.

As used herein, the terms "single chain antibodies" or "single chain Fv (scFv)" refer to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See, e.g., Bird et al., *Science* 242:423-426 (1988) and Huston et al., *Proc. Natl. Acad. Sci. USA* 85:5879-5883 (1988), which is hereby incorporated by reference in its entirety. Such single chain antibodies are included by reference to the term "antibody" fragments, and can be prepared by recombinant techniques or enzymatic or chemical cleavage of intact antibodies.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with a disease or condition.

As used herein the terms "target domain" or "targeting domain" or "targeting moiety" means a polypeptide region bound covalently or non-covalently to a second region within a chimeric molecule, which enhances the concentration of the chimeric molecule or composition in a target sub-cellular location, cell, or tissue relative, as compared to the surrounding locations, cells, and/or tissue.

As used herein, the term "ubiquitination" refers to the attachment of the protein ubiquitin to lysine residues of other molecules. Ubiquitination of a molecule, such as a peptide or protein, can act as a signal for its rapid cellular degradation, and for targeting to the proteasome complex.

As used herein, the terms "ubiquibodies" and "chimeric molecules" are used interchangeably and refer to molecules with at least a degradation domain and a target region, linked by a linker region, as defined herein.

As used herein, the term "variable" refers to the fact that certain segments of the variable domains differ extensively in sequence among antibodies. The V domain mediates antigen binding and defines specificity of a particular antibody for its particular antigen. However, the variability is not evenly distributed across the amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies. See Kabat et al. (1991). The constant domains are not involved directly in binding an antibody to an antigen, but exhibit various effector functions, such as participation of the antibody in antibody dependent cellular cytotoxicity (ADCC).

As used herein, the terms "variant" or "mutant" are used to refer to a protein or peptide which differs from a naturally occurring protein or peptide, i.e., the "prototype" or "wild-type" protein, by modifications to the naturally occurring protein or peptide, but which maintains the basic protein and side chain structure of the naturally occurring form. Such changes include, but are not limited to: changes in one, few, or even several amino acid side chains; changes in one, few or several amino acids, including deletions, e.g., a truncated version of the protein or peptide, insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A "variant" or "mutant" can have enhanced, decreased, changed, or substantially similar properties as compared to the naturally occurring protein or peptide.

One aspect of the present invention relates to an isolated chimeric molecule comprising a degradation domain including a eukaryotic U-box motif and a targeting domain capable of immunospecifically directing the degradation domain to a substrate where the targeting domain is heterologous to the degradation domain. A linker couples the degradation domain to the targeting domain.

The degradation domain contains a U-box motif ubiquitin region, which relates to polypeptides or polypeptide regions capable of modifying substrates by attaching one or more ubiquitin molecules and/or ubiquitin-like molecules to the substrates. In this regard, such a region comports with the well known ubiquitination cascade—involving the coordinated action of the E1, E2, and E3 enzymes—which functions to activate and concomitantly conjugate ubiquitin to a substrate. In some embodiments, the U-box motif is a ubiquitin region composed of an E3 ligase, or fragment thereof, which catalyzes the transfer of ubiquitin in a substrate-specific manner. See Qian et al. (2009).

In some embodiments, the degradation domain of the chimeric molecule lacks an endogenous substrate recognition region, i.e., a portion of the polypeptide that interacts with a natural or native binding partner. The U-box motif of the degradation domain may possess a modified binding domain which inhibits or decreases binding to a substrate compared to the U-box motif without the modified binding region. Nevertheless, the U-box motif permits proteolysis of a substrate in some embodiments. In some embodiments, the modification is a mutation, substitution, or deletion of the binding region. The substitution can be an amino acid substitution such as a conservative or a non-conservative amino acid substitution.

Non-conservative amino acid substitutions of the U-box motif, are substitutions in which an alkyl amino acid is substituted for an amino acid other than an alkyl amino acid in the sequence, an aromatic amino acid is substituted for an amino acid other than an aromatic amino acid in the U-box motif, a sulfur-containing amino acid is substituted for an amino acid other than a sulfur-containing amino acid in the U-box motif, a hydroxy-containing amino acid is substituted for an amino acid other than a hydroxy-containing amino acid in the U-box motif, an acidic amino acid is substituted for an amino acid other than a acidic amino acid in the U-box motif, a basic amino acid is substituted for an amino acid other than a basic amino acid in the U-box motif, or a dibasic monocarboxylic amino acid is substituted for an amino acid other than a dibasic monocarboxylic amino acid in the U-box motif.

Among the common amino acids, for example, "non-conservative amino acid substitutions" are illustrated by a substitution of an amino acids from one of the following groups with an amino acid that is not from the same group, as follows: (1) glycine, alanine, (2) valine, leucine, and isoleucine, (3) phenylalanine, tyrosine, and tryptophan, (4) cysteine and methionine, (5) serine and threonine, (6) aspartate and glutamate, (7) glutamine and asparagine, and (8) lysine, arginine and histidine.

Conservative or non-conservative amino acid changes in, e.g., the U-box motif, can be introduced by substituting appropriate nucleotides for the nucleotides encoding such a region. These modifications can be obtained, for example, by oligonucleotide-directed mutagenesis, linker-scanning mutagenesis, mutagenesis using the polymerase chain reaction, and the like. Ausubel et al., supra; Ausubel et al. (eds.), Short Protocols in Molecular Biology, 5th Edition, John Wiley & Sons, Inc. (2002); see generally, McPherson (ed.), Directed Mutagenesis: A Practical Approach, IRL Press (1991), which are hereby incorporated by reference in their entirety. A useful method for identification of locations for sequence variation is called "alanine scanning mutagenesis" a described by Cunningham and Wells in *Science,* 244:1081-1085 (1989), which is hereby incorporated by reference in its entirety.

Ubiquitin ligase families include, but are not limited to, the homologous to E6-associated protein C-terminus ("HECT") domain ligases, which concerns the transfer of ubiquitin from the E2 conjugase to the substrate, the Really Interesting New Gene ("RING") domain ligases, which bind E2, may mediate enzymatic activity in the E2-E3 complex, and the U-box ubiquitin family of ligases ("UULs"), which constitute a family of modified RING motif ligases without the full complement of $Zn^{2+}$-binding ligands. See Colas et al., "Targeted Modification and Transportation of Cellular Proteins." *Proc Natl Acad Sci USA* 97(25): 13720-5 (2005).

U-box ubiquitin ligases ("ULLs") are characterized as having a protein domain, the U-box, which is structurally related to the RING finger, typical of many other ubiquitin ligases. In humans, the UUL-encoding genes include, but are not limited to, UBE4A and UBE4B genes (also respectively termed UFD2b and UFD2a), CHIP (also termed STUB1), UIP5 (also termed UBOX5), PRP19 (also termed PRPF19 or SNEV), CYC4 (also termed PPIL2 or Cyp-60), WDSUB1, and ACT1 (also termed TRAF3IP2). See Marin, I., "Ancient Origin of Animal U-box Ubiquitin Ligases." *BMC Evolutionary Biology* 10:331, pp. 1-15 (2010), which is hereby incorporated by reference in its entirety.

While HECT E3 ligases have a direct role in catalysis during ubiquitination, RING and U-box E3 proteins facilitate protein ubiquitination by acting as adaptor molecules that recruit E2 and substrate molecules to promote substrate ubiquitination. Although many RING-type E3 ligases, such as MDM2 (murine double minute clone 2 oncoprotein) and c-Cbl, may act alone, others are found as components of much larger multi-protein complexes, such as the anaphase-promoting complex ("APC"). Taken together, these multi-faceted properties and interactions enable E3 enzymes to provide a powerful, and specific, mechanism for protein clearance within all cells of eukaryotic organisms. Ardley et al., "E3 Ubiquitin Ligases." *Essays Biochem.* 41:15-30 (2005), which is hereby incorporated by reference in its entirety.

Functional information concerning the E3 gene products is variable, nonetheless. The U-box protein CHIP acts both as a co-chaperone, together with chaperones such as, e.g., Hsc70, Hsp70 and Hsp90, and as a ubiquitin ligase, alone or as part of complexes that may include other E3 proteins. See id. The selectivity of the ubiquitin proteasome system for a particular substrate nevertheless relies on the interaction between a ubiquitin-conjugating enzyme, e.g., E2, and a ubiquitin-protein ligase. Post-translational modifications of the protein substrate, such as, e.g., phosphorylation or hydroxylation, are often required prior to ubiquitination. In this way, the precise spatio-temporal targeting and degradation for a particular substrate can be achieved.

The U-box motif of the degradation domain disclosed herein possesses a functional E3 ligase that is capable of ubiquitinating a substrate without steric disruption from native binding partners. In addition to the U-box motif, in some embodiments, the degradation domain possesses a ligase that is a RING ligase region, a HECT ligase region, an Anaphase-promoting complex (APC) ligase region, or a U-box ligase region. Such domains may possess cell or tissue specificity. For example, CHIP is highly expressed in skeletal muscle, heart, pancreas, brain, and placenta, while also detected in kidney, liver, and lung. See Ballinger et al. "Identification of CHIP, a Novel Tetratricopeptide Repeat-Containing Protein that Interacts with Heat Shock Proteins and Negatively Regulates Chaperone Functions." *Mol. Cell. Biol.* 19:4535-4545 (1999), which is hereby incorporated by reference in its entirety.

Along these lines, the U-box motif of the chimeric molecule possesses cell-type specific or tissue specific ligase function for, but not limited to, skin cells, muscle cells, epithelial cells, endothelial cells, stem cells, umbilical vessel cells, corneal cells, cardiomyocytes, aortic cells, corneal epithelial cells, somatic cells, fibroblasts, keratinocytes, melanocytes, adipose cells, bone cells, osteoblasts, airway cells, microvascular cells, mammary cells, vascular cells, chondrocytes, placental cells, hepatocytes, glial cells, epidermal cells, limbal stem cells, periodontal stem cells, bone marrow stromal cells, hybridoma cells, kidney cells, pancreatic islets, articular chondrocytes, neuroblasts, lymphocytes, and erythrocytes, or any combination thereof.

In some embodiments, non-limiting examples of E3 ligase regions include E3A, mdm2, UBR5 (EDD1), CHIP (STUB1), LNXp80, CBX4, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RBX1, SMURF1, SMURF2, STUB, TOPORS, TRIP12, UBE3A, UBE3B, UBE3C, UBE4A (UFD2b), UBE4B (UFD2a), UBOX5 (UIP5), UBR5, WWP1, WWP2, ACT1 (TRAF3IP2), PUB19, PRP19 (PRPF19, SNEV), CYC4 (PPIL2, Cyp-60), and WDSUB1. In some embodiments, the U-box motif is selected from E3A, UBR5 (EDD1), CHIP (STUB1), STUB, UBE3A, UBE3B, UBE3C, UBE4A (UFD2b), UBE4B (UFD2a), UBOX5 (UIP5), UBR5, ACT1 (TRAF3IP2), PUB19, PRP19 (PRPF19, SNEV), CYC4 (PPIL2, Cyp-60), and WDSUB1.

Ubiquitin ligase families also include the "F-box" ligases—as in the Skp1-Cullin1-F-box ("SCF") protein complex—which binds to a ubiquitinated substrate, such as, e.g., Cdc 4, which subsequently interacts with a target protein, such as, Sic1 or Grr1, which then binds Cln. See Bai, et al., "SKP1 Connects Cell Cycle Regulators to the Ubiquitin Proteolysis Machinery through a Novel Motif, the F-Box." *Cell* 86 (2): 263-274 (1997), which is hereby incorporated by reference in its entirety.

The F-box is a protein motif of approximately 50 amino acids that functions as a site of protein-protein interaction. See, e.g., Kipreos et al., "The F-box Protein family." *Genome Biol.* 1(5); reviews (2000), which is hereby incorporated by reference in its entirety. F-box proteins were first characterized as components of SCF ubiquitin-ligase complexes, in which they bind substrates for ubiquitin-mediated proteolysis. The F-box motif links the F-box protein to other components of the SCF complex by binding the core SCF component Skp I. F-box proteins have more recently been discovered to function through non-SCF protein complexes in a variety of cellular functions. See id. F-box proteins often include additional carboxy-terminal motifs capable of protein-protein interaction; the most common secondary motifs in yeast and human F-box proteins are WD repeats and leucine-rich repeats, both of which have been found to bind phosphorylated substrates to the SCF complex. See id. The majority of F-box proteins have other associated motifs, and the functions of most of these proteins have not yet been defined. See id.

The least variant positions within the F-box motif include positions 8 (92% of the 234 F-box proteins used for the consensus have leucine or methionine), 9 (92% proline), 16 (86% isoleucine or valine), 20 (81% leucine or methionine), and 32 (92% serine or cysteine). Id. This lack of a strict consensus guides the skilled artisan to employ multiple search algorithms for detecting F-box sequences. Two algorithms, for example, can be found in the Prosite and Pfam databases. Occasionally, one database will give a significant score to an F-box in a given protein when the other does not detect it, so both databases should be searched. Id.

Nevertheless, the configuration of F-box proteins excludes the possibility for intrabody or ubiquitbody engineering. In fact, the amino-terminus of typical intrabodies requires freely accessible variant fragments to preserve antigen binding. See Melchionna et al., "A Protein Silencing Switch by Ligand-induced Proteasome-targeting Intrabodies." *J. Mol. Biol.* 374, 641-654 (2007), which is hereby incorporated by reference in its entirety. Accordingly, the amino-terminus of such protein regions cannot be fused at the carboxy-terminus of F-box proteins, a futile requirement for engineering viable F-box fusion chimeras. Id.

In accord, the chimeric molecules of the present invention possess U-box motif ubiquitin regions attached to targeting domains, which are accessible for substrate binding. In some embodiments, the substrate is an intracellular substrate. In order to facilitate versatility, however, the targeting domain is derived from an antibody, polyclonal antibody, monoclonal antibody, recombinant antibody, antibody fragment, Fab', F(ab')$_2$, Fv, scFv, tascFvs, bis-scFvs, sdAb, VH, VL, Vnar, scFvD10, scFv13R4, humanized antibody, chimeric antibody, complementary determining region (CDR), IgA antibody, IgD antibody, IgE antibody, IgG antibody, IgM antibody, nanobody, intrabody, unibody, minibody, PROTACs, aptameric domains, a ubiquitin binding domain sequence, CHIP binding domain, N-terminal TPR domain, or an E3 binding domain. The skilled artisan will readily appreciate that such targeting domains, in some embodiments, possess cell/tissue specificity in accord with the U-box motif regions described herein.

The targeting domains of the present invention can be monospecific, bispecific, trispecific or of greater multispecificity. Multispecific targeting domains can be specific for different epitopes of a substrate or can be specific for both a substrate polypeptide of the present invention as well as for heterologous compositions, such as a heterologous polypeptide or solid support material. See, e.g., WO 93/17715; WO 92/08802; WO 91/00360; WO 92/05793; Tutt et al., *J. Immunol.* 147:60-69 (1991); U.S. Pat. Nos. 5,573,920, 4,474,893, 5,601,819, 4,714,681, 4,925,648; 6,106,835; Kostelny et al., *J. Immunol.* 148:1547-1553 (1992), which are hereby incorporated by reference in their entirety. The targeting domains of the invention can be from any animal origin, including birds and mammals. For example, the targeting domains may be from human, marine, rabbit, goat, guinea pig, camel, horse, or chicken.

Techniques for generating targeting domains directed to target substrates are well known to those skilled in the art. Examples of such techniques include, but are not limited to, e.g., those involving display libraries, xeno or humab mice, hybridomas, and the like. Target polypeptides—from which a targeting domain is derived—within the scope of the present invention include any polypeptide or polypeptide derivative which is capable of exhibiting antigenicity. Examples include, but are not limited to, substrate and fragments thereof. In some embodiments, the targeting domain is a single-chain antibody.

Single chain antibodies ("scFv") are genetically engineered antibodies that consist of the variable domain of a heavy chain at the amino terminus joined to the variable domain of a light chain by a flexible region. In some embodiments, scFv are generated by PCR from hybridoma cell lines that express monoclonal antibodies (mAbs) with known target specificity, or they are selected by phage display from libraries isolated from spleen cells or lymphocytes, and preserve the affinity of the parent antibody. Employing a protocol to identify intracellular substrates, the yeast two-hybrid technology serves to identify candidate scFv—protein interactions. Such a system is useful to predict whether or not a scFv will be able to recognize its target substrate in vivo. See Pörtner-Taliana et al., "Identification of Protein Single chain Antibody Interactions In Vivo Using Two-hybrid Protocols." *Protein-Protein Interactions: A Molecular Cloning Manual*, Cold Spring Harbor Laboratory Press, Chapter 24 (© 2002), which is hereby incorporated by reference in its entirety.

Typically, scFv, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g., Barbas III et al., *Phage Display, A Laboratory Manual* (Cold Spring Harbor Laboratory Press, Cold Spring Harbor, N.Y., 2001), which is hereby incorporated by reference in its entirety. However, other vector formats could be used for this process, such as cloning the antibody fragment library into a lytic phage vector (modified T7 or Lambda Zap systems) for selection and/or screening.

In general, expression vectors useful in recombinant DNA techniques are often in the form of plasmids. However, the present invention is intended to include such other forms of expression vectors that are not technically plasmids, such as viral vectors, e.g., replication defective retroviruses, adenoviruses and adeno-associated viruses, which serve equivalent functions. Such viral vectors permit infection of a subject and expression in that subject of a compound. The expression control sequences are typically eukaryotic promoter systems in vectors capable of transforming or transfecting eukaryotic host cells. Once the vector has been incorporated into the appropriate host, the host is maintained under conditions suitable for high level expression of the nucleotide sequences encoding the target domain, and the collection and purification of the substrate binding agent, e.g., cross-reacting anti-substrate antibodies. See, generally, U.S. Patent Publication No. 2002/0199213, which is hereby incorporated by reference in its entirety. Vectors can also encode signal peptide, e.g., pectate lyase, useful to direct the secretion of extracellular antibody fragments. See U.S. Pat. No. 5,576,195, which is hereby incorporated by reference in its entirety.

Expression of the chimeric molecules of the present invention in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression; (ii) to increase the solubility; and (iii) to aid in purification by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their endogenous recognition sequences, include Factor Xa, thrombin and enterokinase. Typical fusion expression vectors include pGEX (Pharmacia Biotech Inc; Smith and Johnson, Gene 67:31-40 (1988), which is hereby incorporated by reference in its entirety), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., Gene 69:301-315 (1988) and pET 11d (Studier et al., *Gene Expression Technology: Methods In Enzymology* 185, Academic Press, San Diego, Calif. 60-89 (1990)), which are hereby incorporated by reference in their entirety. Methods for targeted assembly of distinct active peptide or protein domains to yield multifunctional polypeptides via polypeptide fusion has been described by Pack et al., U.S. Pat. Nos. 6,294,353; 6,692,935, which are hereby incorporated by reference in their entirety. One strategy to maximize recombinant polypeptide expression, e.g., a chimeric molecule of the present invention, in *E. coli* is to express the polypeptide in host bacteria with an impaired capacity to proteolytically cleave the recombinant chimera. See, e.g., Gottesman, *Gene Expression Technology: Methods In Enzymology* 185, Academic Press, San Diego, Calif. 119-128 (1990), which is hereby incorporated by reference in its entirety.

In some embodiments, a nucleic acid encoding a chimeric molecule of the present invention—including a degradation domain and a targeting region—is expressed in mammalian cells using a mammalian expression vector. Examples of mammalian expression vectors include, e.g., but are not limited to, pCDM8 (Seed, *Nature* 329:840 (1987)), and pMT2PC (Kaufman, et al., *EMBO J.* 6:187-195 (1987)), which are hereby incorporated by reference in their entirety. When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the targeting domains, degradation domains of the chimeric molecule. See, e.g., Chapters 16 and 17 of Sambrook, et al., *Molecular Cloning: A Laboratory Manual.* 2nd ed., Cold Spring Harbor Laboratory, Cold Spring Harbor Laboratory Press, Cold Spring Harbor, N.Y., (1989), which are hereby incorporated by reference in their entirety.

Notwithstanding chimeric molecule U-box degradation domains and targeting domain expression, the function of such domains/regions imparts the immunospecificity of the present invention. A known or unknown substrate is bound by the targeting domain for subsequent ubiquitination via the degradation domain. In some embodiments, the substrates include, but are not limited to, intracellular substrates, extracellular substrates, modified substrates, glycosylated substrates, farnesylated substrates, post translationally modified substrates, phosphorylated substrates, and other modifications known in the art.

In some embodiments, the substrates include, but are not limited to, β-galactosidase, gpD, Hsp70, post-translationally modified proteins, fibrillin, huntingtin, tumorigenic proteins, p53, Rb, adhesion proteins, receptors, cell-cycle proteins, checkpoint proteins, HFE, ATP7B, prion proteins, viral proteins, bacterial proteins, parasitic proteins, fungal proteins, DNA binding proteins, metabolic proteins, regulatory proteins, structural proteins, enzymes, immunogenic proteins, auto-immunogenic proteins, immunogens, antigens, pathogenic proteins, and the like.

Although targeting domains possess intrinsic binding interactions, e.g., secondary, tertiary or quaternary flexibility, there must still be flexibility with respect to the association with the U-box motif ubiquitin region. In this regard, absence adequate spacing, it is possible for the U-box motif to sterically hinder the substrate-target domain interaction. As such, the present invention employs polypeptide linkers of sufficient length to prevent the steric disruption of binding between the targeting domain and the substrate, in some embodiments.

In some embodiments, the targeting domain is covalently attached to the ubiquitin region via a linker that may be cleavable or non-cleavable under physiological conditions. The linker can entail an organic moiety comprising a nucleophilic or electrophilic reacting group which allows covalent attachment to the targeting domain to the ubiquitin region agent. In some embodiments, the linker is an enol ether, ketal, imine, oxime, hydrazone, semicarbazone, acylimide, or methylene radical. The linker may be an acid-cleavable linker, a hydrolytically cleavable linker, or enzymatically-cleavable linker, in some embodiments.

Peptide-based linking groups are cleaved by enzymes such as peptidases and proteases in cells. Peptide-based cleavable linking groups are peptide bonds formed between amino acids to yield oligopeptides, e.g., dipeptides, tripeptides, and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond, i.e., the amide bond, formed between amino acids yielding peptides and proteins and does not include the entire amide functional group. Peptide cleavable linking groups have the general formula —NHCHR1C(O) NHCHR2C(O)—, where R1 and R2 are the R groups of the two adjacent amino acids. These candidates can be evaluated using methods analogous to those described above.

For in vitro applications, appropriate linkers, which can be cross-linking agents for use for conjugating a polypeptide to a solid support, include a variety of agents that can react with a functional group present on a surface of the support, or with the polypeptide, or both. Reagents useful as cross-linking agents include homo-bi-functional and, in particular, hetero-bi-functional reagents. Useful bi-functional cross-linking agents include, but are not limited to, N-SIAB, dimaleimide, DTNB, N-SATA, N-SPDP, SMCC and 6-HYNIC. A cross-linking agent can be selected to provide a selectively cleavable bond between a polypeptide and the solid support. For example, a photolabile cross-linker, such as 3-amino-(2-nitrophenyl)propionic acid can be employed as a means for cleaving a polypeptide from a solid support. See Brown et al., *Mol. Divers* 4-12 (1995); Rothschild et al., *Nucl. Acids Res.* 24:351-66 (1996); and U.S. Pat. No. 5,643,722), which are hereby incorporated by reference in their entirety.

An antibody, polypeptide, or fragment thereof, such as a targeting domain, can be immobilized on a solid support, such as a bead, through a covalent amide bond formed between a carboxyl group functionalized bead and the amino terminus of the polypeptide or, conversely, through a covalent amide bond formed between an amino group functionalized bead and the carboxyl terminus of the polypeptide. In addition, a bi-functional trityl linker can be attached to the support, e.g, to the 4-nitrophenyl active ester on a resin, such as a Wang resin, through an amino group or a carboxyl group on the resin via an amino resin. Using a bi-functional trityl approach, the solid support can require treatment with a volatile acid, such as formic acid or trifluoracetic acid to ensure that the polypeptide is cleaved and can be removed. In such a case, the polypeptide can be deposited as a beadless patch at the bottom of a well of a solid support or on the flat surface of a solid support. After addition of a matrix solution, the polypeptide can be desorbed into a MS.

It will be readily apparent to the skilled artisan that the methods and techniques described above can be employed for the chimeric molecule of the present invention, including its constituent parts, e.g., degradation domains, ubiquitin regions, target regions, and modifications thereof, as well as the linker molecules, as described above.

One aspect of the present invention relates to a composition comprising the chimeric molecule and a pharmaceutically-acceptable carrier. According to the methods of the present invention, the chimeric molecule can be incorporated into pharmaceutical compositions suitable for administration.

The pharmaceutical compositions generally entail recombinant or substantially purified chimeric molecules and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the protein compositions. See, e.g., *Remington's Pharmaceutical Sciences*, Mack Publishing Co., Easton, Pa. 18*th* ed. (1990), which is hereby incorporated by reference in its entirety. The pharmaceutical compositions are generally formulated as sterile, substantially isotonic and in full compliance with all Good Manufacturing Practice (GMP) regulations of the U.S. Food and Drug Administration.

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The compositions of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compositions may be incorporated with excipients and used in the form of tablets, capsules, elixirs, suspensions, syrups, and the like. Such compositions and preparations should contain at least 0.1% of active compound. The percentage of the composition in these compositions may, of course, be varied and may conveniently be between about 2% to about 60% of the weight of the unit. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

These compositions may also be administered parenterally. Solutions or suspensions of the present compositions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The composition of the present invention may also be administered directly to the airways in the form of an aerosol. For use as aerosols, the compositions of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compositions of the present invention further contain, in some embodiments, a second agent or pharmaceutical composition selected from the non-limiting group of anti-inflammatory agents, antidiabetic agents, hpyolipidemic agents, chemotherapeutic agents, antiviral agents, antibiotics, metabolic agents, small molecule inhibitors, protein kinase inhibitors, adjuvants, apoptotic agents, proliferative agents, organotropic targeting agents, immunological agents, antigens from pathogens, such as viruses, bacteria, fungi and parasites, optionally in the form of whole inactivated organisms, peptides, proteins, glycoproteins, carbohydrates, or combinations thereof, any examples of pharmacological or immunological agents that fall within the above-mentioned categories and that have been approved for human use that may be found in the published literature, any other bioactive component, or any combination of any of these.

In some embodiments, a second agent or pharmaceutical composition selected from the non-limiting group of anti-inflammatory agents, antidiabetic agents, hpyolipidemic agents, chemotherapeutic agents, antiviral agents, antibiotics, metabolic agents, small molecule inhibitors, protein kinase inhibitors, adjuvants, apoptotic agents, proliferative agents, organotropic targeting agents.

The importance of E3 ligases, and functional domains thereof, is highlighted by the number of normal cellular processes they regulate, and underlies the attendant diseases associated with loss of function or inappropriate targeting. See Ardley et al., "E3 Ubiquitin Ligases. *Essays Biochem.*" 41:15-30 (2005), which is hereby incorporated by reference in its entirety. For example, recessive mutations in the parkin gene are a well-known cause of familial Parkinson disease, and therefore it is of significant interest that CHIP also interacts with the products of several other familial Parkinson disease genes, such as SNCA (which encodes α-synuclein; and LRRK2. Id. The involvement of CHIP in interacting and/or ubiquitinating other proteins also implicates nervous system and neurodegenerative diseases, such as Tau and APP (Alzheimer disease), Malin (Lafora disease) and ataxin-1 and ataxin-3 (associated respectively to spinocerebellar ataxia types 1 and 3). See id. Consistent with a highly pleiotropic phenotype, CHIP null mutant mice show shortened life span, accelerated aging and anomalous oxidative stress and protein quality levels. See Marin, I., "Ancient Origin of Animal U-box Ubiquitin Ligases." *BMC Evolutionary Biology* 10:331, pp. 1-15 (2010), which is hereby incorporated by reference in its entirety.

In one aspect, the present invention relates to methods of treating a disease. In some embodiments, the method of treating a disease involves administering the composition to a subject having a disease, where the subject to whom the composition is administered has an increased expression level of a substrate compared to a subject not afflicted with the disease.

The methods may involve administering compositions to a subject, where the disease possesses a measurable phenotype. The phenotype of the disease involves an increased expression level of a substrate compared to the phenotype from a subject not afflicted with the disease, in some embodiments. In this respect, chimeric molecules contained in the pharmaceutical compositions of the present invention are efficacious against treating or alleviating the symptoms from a disease characterized by a phenotypic increase in the expression level of one or more substrates compared to the phenotype from a subject not afflicted with the disease.

Non-limiting examples of diseases that can be treated or prevented in the context of the present invention, include, cancer, metastatic cancer, solid cancers, invasive cancers, disseminated cancers, breast cancer, lung cancer, NSCLC cancer, liver cancer, prostate cancer, brain cancer, pancreatic cancer, lymphatic cancer, ovarian cancer, endometrial cancer, cervical cancer, and other solid cancers known in the art, blood cell malignancies, lymphomas, leukemias, myelomas, stroke, ischemia, myocardial infarction, congestive heart failure, stroke, ischemia, peripheral vascular disease, alcoholic liver disease, cirrhosis, Parkinson's disease, Alzheimer's disease, diabetes, cancer, arthritis, ALS, pathogenic diseases, idiopathic diseases, viral diseases, bacterial, diseases, prionic diseases, fungal diseases, parasitic diseases, arthritis, wound healing, immunodeficiency, inflammatory disease, aplastic anemia, anemia, genetic disorders, congenital disorders, type 1 diabetes, type 2 diabetes, gestational diabetes, high blood glucose, metabolic syndrome, lipodystrophy syndrome, dyslipidemia, insulin resistance, leptin resistance, atherosclerosis, vascular disease, hypercholesterolemia, hypertriglyceridemia, non-alcoholic fatty liver disease, septic shock, multiple organ dysfunction syndrome, rheumatoid arthritis, trauma, stroke, heart infarction, systemic autoimmune disease, chronic hepatitis, overweight, and/or obesity, or any combination thereof.

In some embodiments, the disease is cancer, metastatic cancer, stroke, ischemia, peripheral vascular disease, alcoholic liver disease, hepatitis, cirrhosis, Parkinson's disease, Alzheimer's disease, cystic fibrosis diabetes, ALS, pathogenic diseases, idiopathic diseases, viral diseases, bacterial, diseases, prionic diseases, fungal diseases, parasitic diseases, arthritis, wound healing, immunodeficiency, inflammatory disease, aplastic anemia, anemia, genetic disorders, congenital disorders, type 1 diabetes, type 2 diabetes, gestational diabetes, high blood glucose, metabolic syndrome, lipodystrophy syndrome, dyslipidemia, insulin resistance, leptin resistance, atherosclerosis, vascular disease, hypercholesterolemia, hypertriglyceridemia, non-alcoholic fatty liver disease, overweight, or obesity, and any combination thereof.

When used in vivo for therapy, the compositions are administered to the subject in effective amounts, i.e., amounts that have desired therapeutic effect. The dose and dosage regimen will depend upon the degree of the disease in the subject, the characteristics of the particular peptide used, e.g., its therapeutic index, the subject, and the subject's history. The effective amount may be determined during pre-clinical trials and clinical trials by methods familiar to physicians and clinicians. An effective amount of a peptide useful in the methods may be administered to a mammal in need thereof by any of a number of well-known methods for administering pharmaceutical compounds.

Dosage, toxicity and therapeutic efficacy of the compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices may be desirable. While compositions that exhibit toxic side effects may be used, care should be taken to design a delivery system that targets such compositions to the site of affected tissue in order to minimize potential damage to uninfected cells and, thereby, reduce side effects.

In some embodiments, the compositions of the present invention are administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes.

In one aspect, the present invention relates to a method for substrate silencing. The method involves selecting a substrate to be silenced and providing a chimeric molecule. The substrate and the chimeric molecule are contacted under conditions to permit the formation of a substrate-molecule complex, where the complex mediates the degradation of the substrate to be silenced. In some embodiments, the complex mediates the degradation by post-translational ubiquitination of the substrate. The methods involve silencing one or more substrates previous described herein.

One aspect of the present invention relates to screening agents for therapeutic efficacy against a disease. This method involves providing a biomolecule whose presence is mediated by a disease state. A test agent composed of (i) a degradation domain including a eukaryotic U-box motif, (ii) a targeting domain capable of immunospecifically directing the degradation domain to the biomolecule, where the targeting domain is heterologous to the degradation domain, and (iii) a linker coupling the degradation domain to the targeting domain are provided. The biomolecule and the test agent are contacted under conditions effective for the test agent to facilitate degradation of the biomolecule. The level of the biomolecule, as a result of the contacting, is determined and the test agent which, based on the determining, decreases the level of the biomolecule is identified as being a candidate for therapeutic efficacy against the disease.

In some embodiments, the identifying is carried out with respect to a standard biomolecule level in a subject not afflicted with the disease. The identifying may also be carried out with respect to the biomolecule level absent the contacting, in some embodiments. A control level, in the regard, can be employed to compare to the level of the biomolecule in a sample. In some embodiments, the control level is the level of the biomolecule from a subject not afflicted with the disease. An overabundance of the biomolecule in the sample obtained from the subject suspected of having the disease or condition affecting substrate levels compared with the sample obtained from the healthy subject is indicative of the biomolecule-associated disease or condition in the subject being tested.

There are a myriad of diseases in which the degree of overabundance of certain substrate biomolecules are known to be indicative of whether a subject is afflicted with a disease or is likely to develop a disease. See, e.g., Anderson et al., Discovering Robust Protein Biomarkers for Disease from Relative Expression Reversals in 2-D DIGE Data."

*Proteomics.* 7, 1197-1207 (2007), which is hereby incorporated by reference in its entirety. Examples of conditions in which biomolecules are increased compared to control subjects include the diseases described above.

Accordingly, the chimeric molecules and compositions of the present invention are administered to a subject in need of treatment. U-box ubiquitin ligases, such as the E3 gene products encoding a U-box motif, are described above, and can be used in the present screening methods for determining the efficacy of the chimeric molecules disclosed herein. In some embodiments, suitable in vitro or in vivo assays are performed to determine the effect of the chimeric molecules and compositions of the present invention and whether administration is indicated for treatment. Compositions for use in therapy can be tested in suitable animal model systems including, but not limited to rats, mice, chicken, cows, monkeys, rabbits, and the like, prior to testing in human subjects. Similarly, for in vivo testing, any of the animal model system known in the art can be used prior to administration to human subjects.

Any method known to those in the art for contacting a cell, organ or tissue with a composition may be employed. In vivo methods typically include the administration of a chimeric molecule or composition, such as those described above, to a mammal, suitably a human. When used in vivo for therapy, the chimeric molecules or compositions are administered to the subject in effective amounts, as described herein. Results can be ascertained as per the empirical variables set forth at the outset of the methods described herein.

In vitro methods typically include the assaying the effect of chimeric molecule or composition, such as those described above, on a sample or extract. In some embodiments, chimeric molecule efficacy can be determined by assessing the affect on substrate degradation, i.e., the ability of the chimeric molecules and compositions to exert a phenotypic change in a sample. Such methods include, but are not limited to, immunohistochemistry, immunofluorescence, ELISPOT, ELISA, or RIA. The steps of various useful immunodetection methods have been described in the scientific literature, such as, e.g., Maggio et al., *Enzyme-Immunoassay*, (1987) and Nakamura, et al., Enzyme Immunoassays: Heterogeneous and Homogeneous Systems, Handbook of Experimental Immunology, Vol. 1: *Immunochemistry*, 27.1-27.20 (1986), each of which is incorporated herein by reference in its entirety and specifically for its teaching regarding immunodetection methods.

Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), enzyme linked immunospot assay (ELISPOT), radioimmunoassays (RIA), radioimmune precipitation assays (RIPA), immunobead capture assays, Western blotting, dot blotting, gel-shift assays, Flow cytometry, immunohistochemistry, fluorescence microscopy, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomolecule) with an antibody to the molecule of interest or contacting an antibody to a molecule of interest (such as antibodies to the disclosed biomolecule) with a molecule that can be bound by the antibody, as the case may be, under conditions effective to allow the formation of immunocomplexes. In this regard, the skilled artisan will be able to assess the presence and or level of specific biomolecules in a given sample. Subsequently, the chimeric molecule compositions of the present invention are added to the assay. Thereafter, the level of biomolecule can be assessed, i.e., the presence or level thereof, using the immunoassays described herein to determine the post-treatment phenotypic effect.

Immunoassays can include methods for detecting or quantifying the amount of a biomolecule of interest in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety and specifically for teachings regarding immunodetection methods and labels.

The treatment methods of the present technology possess ubiquitin regions attached to targeting domains, as described above. In some embodiments, the targeting domain binds an intracellular biomolecule, as described above. Likewise, the treatment methods of the present invention employ polypeptide linkers of sufficient length to prevent the steric disruption of binding between the targeting domain and the substrate. In some embodiments, the biomolecule is associated with a disease as described above.

Another aspect of the present invention relates to screening for disease biomarkers. This method involves providing a sample of diseased cells expressing one or more ligands. A plurality of chimeric molecules composed of (i) a degradation domain including a eukaryotic U-box motif, (ii) a targeting domain capable of immunospecifically directing the degradation domain to the one or more ligands, where the targeting domain is heterologous to the degradation domain, and (iii) a linker coupling the degradation domain to the targeting domain. The sample and the plurality of chimeric molecules are contacted under conditions effective for the diseased cells to fail to proliferate in the absence of the chimeric molecule. The chimeric molecules which permit the diseased cells to proliferate are determined, and the ligands which bind to the chimeric molecules determined to permit diseased cells to proliferate, are identified as biomarkers.

Many, if not all diseases, are complex and multifactorial. When considering neurodegeneration, for example, substantial neuronal cell loss occurs before pathologic presentation. Screening for and developing such drugs—to treat neurodegenerative diseases—is further stymied by ancillary therapies which ameliorate the symptoms. Thus, target detection is obfuscated by prior therapeutic administration, which, may in turn, slow disease progression and further confound treatment regimes. In this way, the present invention provides new, inventive, screening methods for elucidation of disease biomarkers by employing phenotypic screening analyses. See, e.g., Pruss, R. M., "Phenotypic Screening Strategies for Neurodegenerative Diseases: A Pathway to Discover Novel Drug Candidates and Potential Disease Targets or Mechanisms." *CNS & Neurological Disorders—Drug Targets,* 9, 693-700 (2010), which is hereby incorporated by reference in its entirety.

Phenotypic screening involves using an appropriate sample, e.g., class of cells, cell extract, neurons, tissue, and the like, from a patient afflicted with a disease and subjecting the sample to one or more chimeric molecules as described herein. Subsequently, the sample is screened for viability, proliferation, cell processes and/or phenotypic characteristic of the diseased cell, e.g., shrinking, loss of membrane potential, morphological changes, and the like. See id. Image analysis software allows for cell bodies or other objects to empirically assess the results. Hits coming from the screen may maintain cell survival by stimulating survival pathways, mimicking trophic factors, or inhibiting death signaling. Higher content screening and profiling in target-directed secondary assays can then be used to identify targets and mechanisms of action of promising hits.

Examples of diseases conditions from which a biomarker screening analysis can be performed include the diseases described above. In some embodiments, the method of screening for disease biomarkers includes a plurality of molecules, where the molecules possess a U-box motif as described above. In some embodiments, the biomarker screening methods include molecules possessing a targeting domain as described above. The screening methods of the present technology employ polypeptide linkers of sufficient length to prevent the steric disruption of binding between the targeting domain and the ligand.

Once a chimeric molecule is determined to provide a therapeutic indication, the biomarker is isolated using the targeting domain region (or the entire chimeric molecule) to immunoprecipitate the biomarker, from a sample, which is subsequently identified using methods well known in the art. Biomarker isolation and purification methods include, but are not limited to, for example, HPLC or FPLC chromatography using size-exclusion or affinity-based column resins. See, e.g., Sambrook, et al. 1989, Cold Spring Harbor Laboratory Press, which is hereby incorporated by reference in its entirety.

Active fragments, derivatives, or variants of the polypeptides of the present invention may be recognized by, for example, the deletion or addition of amino acids that have minimal influence on the properties, secondary structure, and biological activity of the polypeptide. For example, a polypeptide may be joined to a signal (or leader) sequence at the N-terminal end of the protein which co-translationally or post-translationally directs sub-cellular or extracellular localization of the protein.

The biomarker can then be elucidated using techniques known in the art. In some embodiments, determining the identity of the biomarker is performed using MALDI-TOF, mass spectrometry, mass spectroscopy, protein sequencing, antibody interactions, western blot, immunoassay, ELISA, chromatographic techniques, reverse proteomics, immunoprecipitations, radioimmunoassay, and immunofluorescence, or any combinations thereof.

Suitable mass spectrometric techniques for the study and identification of proteins include, laser desorption ionization mass spectrometry and electrospray ionization mass spectrometry. Within the category of laser desorption ionization (LDI) mass spectrometry (MS), both matrix assisted LDI (MALDI) and surface assisted LDI (SELDI) time-of-flight (TOF) MS may be employed. SELDI TOF-MS is particularly well-suited for use in the present methods because it provides attomole sensitivity for analysis, quantification of low abundant proteins (pg-ng/ml) and highly reproducible results.

The methods described herein can be performed, e.g., by utilizing pre-packaged kits comprising at least one reagent, e.g., a chimeric molecule or composition described herein, which can be conveniently used, e.g., in clinical settings to treat subjects exhibiting symptoms of a disease or illness involving an overexpressed substrate, biomolecule, or biomarker. Furthermore, any cell type or tissue in which the chimeric molecule of the present invention can be expressed is suitable for use in the kits described herein.

In another aspect of the present invention, a kit or reagent system for using the chimeric molecules and compositions of the present invention. Such kits will contain a reagent combination including the particular elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit may be adapted for any configuration of an assay and may include compositions for performing any of the various assay formats described herein.

Reagents useful for the disclosed methods can be stored in solution or can be lyophilized. When lyophilized, some or all of the reagents can be readily stored in microtiter plate wells for easy use after reconstitution. It is contemplated that any method for lyophilizing reagents known in the art would be suitable for preparing dried down reagents useful for the disclosed methods.

Also within the scope of the invention are kits comprising the chimeric molecules/compositions and second agents of the invention and instructions for use. The kits are useful for detecting the presence of a substrate in a biological sample e.g., any body fluid including, but not limited to, e.g., serum, plasma, lymph, cystic fluid, urine, stool, cerebrospinal fluid, acitic fluid or blood and including biopsy samples of body tissue. For example, the kit can comprise one or more chimeric molecules composed of a U-box motif ubiquitin region linked to a targeting domain capable of binding a substrate in a biological sample.

EXAMPLES

The Examples set forth below are for illustrative purposes only and are not intended to limit, in any way, the scope of the present invention.

The following examples are included to demonstrate illustrative embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Plasmids

For prokaryotic expression of ubiquibodies, pET28a with C-terminal FLAG and His6 tags was used. CHIP and CHIPΔTPR were cloned from pET30a-hCHIP-His6. scFv13 and scFv13R4 were cloned from pET-scFv13(R4)-SecM17 vectors (see Contreras-Martinez, et al., "Intracellular Ribosome Display via SecM Translation Arrest as a Selection for Antibodies with Enhanced Cytosolic Stability." *J Mol Biol*

372(2): 513-24 (2007)), which is hereby incorporated by reference in its entirety, while and scFvD10 was cloned from pHK49-gpD-specific antibody D10. See Koch et al., "Direct Selection of Antibodies from Complex Libraries with the Protein Fragment Complementation Assay." *J Mol Biol* 357(2): 427-41 (2006), which is hereby incorporated by reference in its entirety. scFvs were cloned between NcoI and EcoRI sites, followed by a Gly-Ser-Gly-Ser-Gly (SEQ ID NO: 1) linker that was inserted by PCR before CHIPΔTPR followed by a SalI site. The FLAG and His6 tags were created by primer dimerization and inserted between SalI and HindIII sites. For expression of the antigen gpD, pET28a, with N-terminal His6 and HA tags between NcoI and NdeI sites, was used and gpD was cloned from pHK43-gpD (Koch et al. 2006) between NdeI and HindIII. The point mutant H260Q was made using the QuikChange® Site-Directed Mutagenesis Kit (Stratagene).

For eukaryotic expression, ubiquibodies were cloned into pcDNA3 between HindIII and XbaI sites with the modification of including the human Kozak sequence surrounding the ATG start codon (accATGg). The antigen β-gal was expressed using pCMV-β-gal (provided by Pengbo Zhou) and HA-tagged gpD was similarly cloned into pCMV using the flanking NotI sites.

Example 2—Antibodies and Reagents

Mouse monoclonal [M2] to DDDDK tag (HRP) from Abcam (ab49763) was used to probe for ubiquibodies while rabbit anti-HA produced by Sigma (H6908) was used to probe the antigen gpD and rabbit polyclonal anti-β-gal from Abcam (ab616) was used to probe the antigen β-gal. Rabbit polyclonal anti-ubiquitin from Abcam (ab8134) and rabbit anti-ubiquitin Lys48-specific from Millipore (clone Apu2) were used to detect poly-ubiquitin chains. Mouse monoclonal anti-HSP70 from Enzo Life Sciences (C92F3A-5) and mouse monoclonal anti-GFP from Roche were used as controls for the eukaryotic expression. All of the above were used with secondary antibodies from Promega, anti-mouse-HRP and anti-rabbit-HRP.

Example 3—In Vitro Reconstitution Assays

Purified ubiquitin and ubiquitin activating enzyme (E1) were purchased from Boston Biochem, ubiquitin conjugating enzyme (E2, UbcH5a) was purchased from Millipore, Hsp70 was purchased from Enzo Life Sciences and β-gal was purchased from Sigma. Moreover, in vitro ubiquitination assays were performed in the presence of 20 mM MOPS pH 7.2, 100 mM KCl, 5 mM MgCl2 1 mM DTT, 4 mM ATP, 50 μM ubiquitin, 0.1 μM E1, 2 μM E2, 3 μM E3 (ubiquibody or control protein) and 3 μM target protein ((β-gal, gpD or Hsp70). Reactions were carried out at 37° C. and analyzed by SDS-PAGE and immunoblotting.

Example 4—Expression and Purification of Proteins

Soluble expression was evaluated by growing bacteria at 37° C. to an OD600 of 0.4-0.6 before induction with 1 mM IPTG followed by continued growth at 30° C. for 6 hours before harvesting. Cells were then lysed by Bugbuster (Novagen®) and the soluble fraction of cellular lysates was evaluated by Western blotting to determine the relative expression levels. For purification, cell cultures were grown as described, although cells were mechanically lysed by sonication in order to avoid chemical contamination. Proteins were purified utilizing Ni-NTA spin columns (Qiagen®) that contain Ni-NTA silica in pre-packed columns compatible with a microcentrifuge. Purified protein elutions ranged from 2-13 mg/mL, were used immediately for ELISA analysis and stored long-term at −20C in 25% glycerol.

Example 5—Enzyme-Linked Immunosorbent Assays (ELISAs

Briefly, ELISAs were performed using a 96-well plate coated with antigen (β-gal, gpD or Hsp70) at a concentration of 10 μg/mL (1 μg of antigen per well) and incubated overnight at 4° C. After blocking with BSA for 2 hours at RT, the purified ubiquibody was applied to each well over a concentration range of 4 μg-32 ng per well (in triplicate). Following a one-hour incubation, the plate was washed and probed for bound ubiquibodies with anti-flag-HRP antibody for one-hour. The amount of bound anti-flag-HRP was determined by using SigmaFAST™ o-phenylenediamine dihydrochloride (OPD) tablets for detection of peroxidase activity at 492 nm.

Example 6—In Vivo Expression

HEK293T cells were incubated in 6 cm petri dishes at 37° C. under 5% $CO_2$ until reaching 60-70% confluency. Calcium phosphate transient transfection was performed by mixing 12 μg of DNA with $CaCl_2$ and 2×HBS (HEPES buffered saline) while vortexing. Each DNA preparation contained 2 μg of pCMV-HA-gpD, 0.5 μg of pGFP and varying amounts of pcDNA3-uAb with pcDNA3 to total 12 ug per dish. The calcium phosphate mixture was then added to the cells dropwise and allowed to incubate with the cells for 24 hrs. 48 hrs post-transfection the cells were harvested and lysed with NP-40 lysis buffer for SDS-PAGE and immunoblotting analysis.

Example 7—Ubiquibody Efficacy

Figure 6:
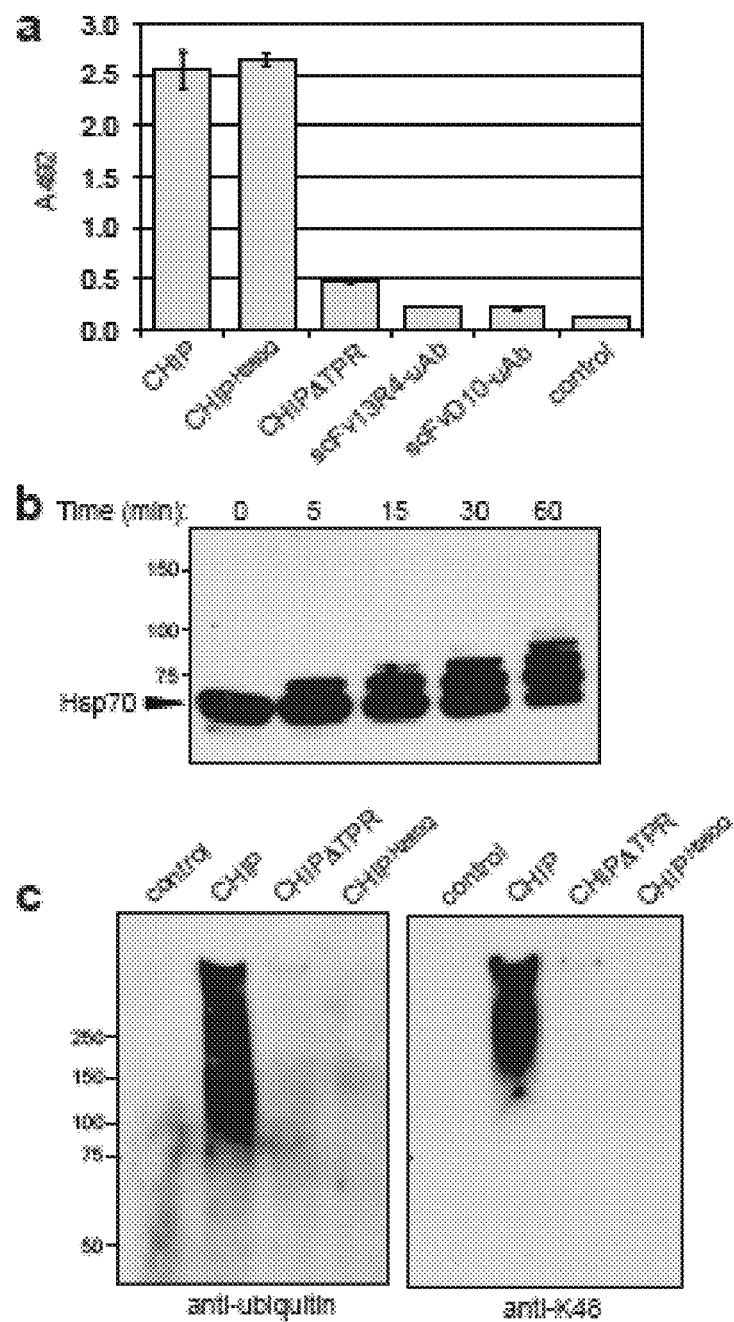
FIGS. 6A-C show the binding and ubiquitination of Hsp70 by CHIP.

Ubiquibodies were first produced in *E. coli* and purified to test their functionality in vitro. This was performed by cloning the scFv of interest, a Gly-Ser-Gly-Ser-Gly (SEQ ID NO: 1) linker, and human CHIP (C-terminus of Hsc70-interacting protein) without its N-terminal TPR domain, into a pET28a plasmid with C-terminal FLAG and 6×His tags. See FIG. 1A and Table 1 containing the sequence data. Plasmids were then transformed into *E. coli* BL21(DE3), induced at an OD600 of 0.4 with 1 mM IPTG and grown at 30° C. for 6 hours. As shown in FIG. 1B, soluble ubiquibody expression containing scFv13R4 (Martineau et al. (1998)) and scFvD10 (Koch et al. (2006)), bound to β-galactosidase (β-gal) and gpD, respectively. These ubiquibodies (and controls—CHIP, CHIPΔTPR, and scFv13R4) were subsequently purified from cell lysates using Ni-NTA spin columns (Qiagen®). To determine the relative binding affinity for β-gal, purified samples were analyzed using ELISA. See FIG. 1C. Only constructs containing the endogenous scFv13R4 bound the antigen. The CHIPΔTPR domain alone was unable to bind its native substrate Hsp70 (see FIG. 6A) or β-gal. See FIG. 1C. In vitro ubiquitination assays were performed to assess whether the scFv13R4-uAb was able to bind β-gal. In short, ubiquitin components (0.1 μM E1, 2 μM E2, 3 μM scFv13R4-uAb and 3 μM β-gal), in the presence of ATP, were incubated at 37° C., and FIG. 2A shows the results using 50 μM ubiquitin.

Figure 2:
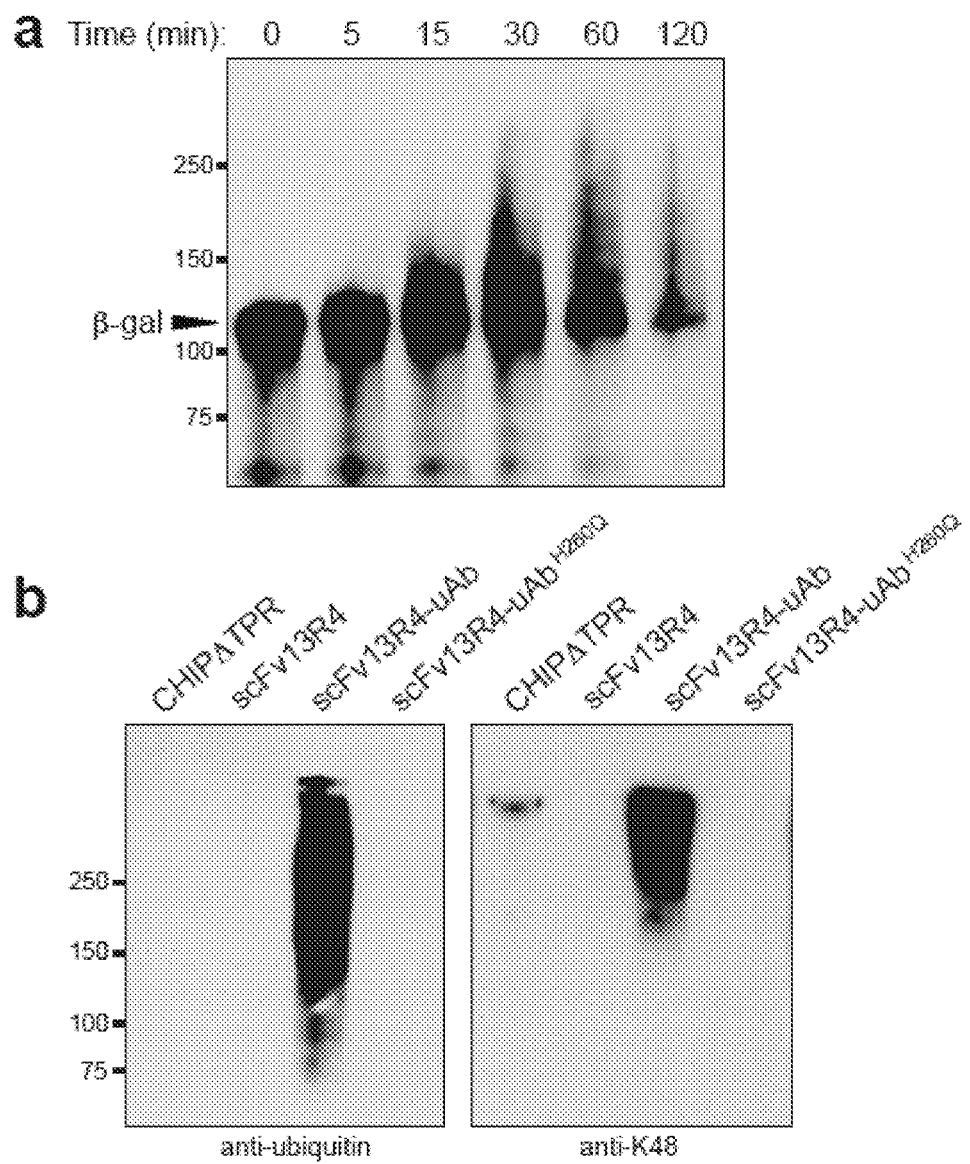
FIGS. 2A-B are SDS-PAGE gels from in vitro ubiquitination of β-galactosidase.
Figure 3:
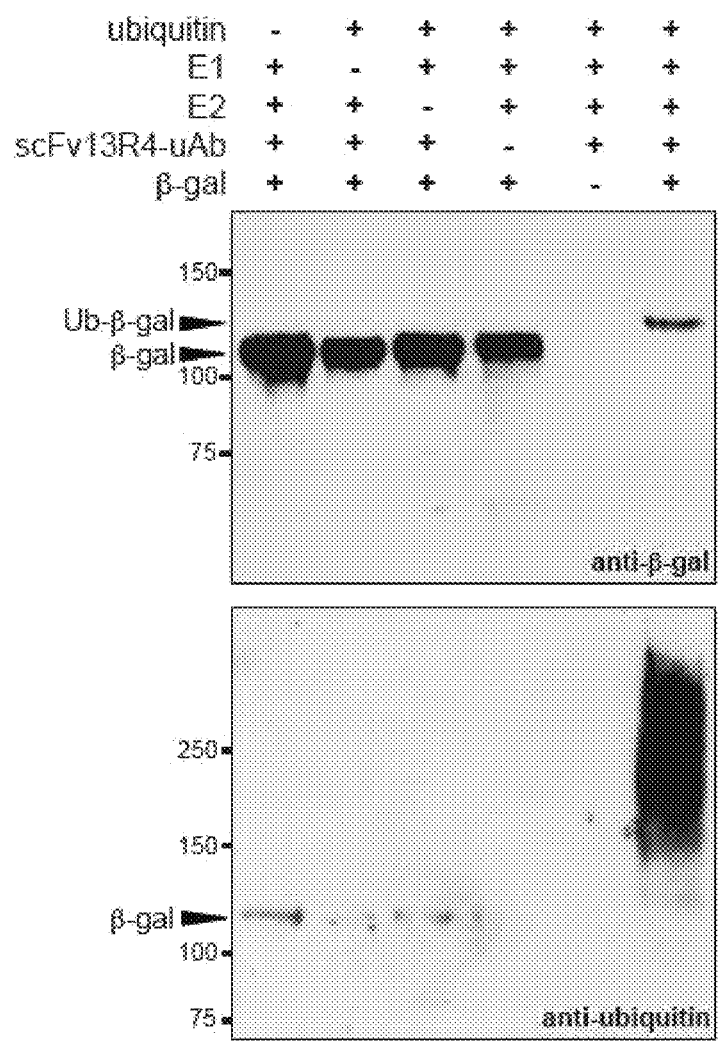
FIG. 3 is a western blot from an in vitro ubiquitin assay that illustrates the cascade-dependent ubiquitination of β-galactosidase. β-gal and scFv13R4-uAb in vitro ubiquitination reactions were performed in the absence of individual elements required for the ubiquitination cascade. The reactions were incubated at 37° C. for 2 hours and samples were analyzed using 8% SDS-PAGE followed by immunobloting with anti-β-gal antibodies (upper panel). The blot was subsequently washed and re-probed with anti-ubiquitin antibodies (lower panel).

The laddering effect shown in FIG. 2A represents the addition of ubiquitin molecules (8.4 kDa) to β-gal (116 kDa). These results are similar to what was observed when Hsp70 is assayed for CHIP-mediated ubiquitination. See FIG. 6B. FIG. 2B shows reactions containing control molecules CHIPΔTPR, scFv13R4 and scFv13R4-uAbH260Q, which were unable to ubiquinate β-gal. In fact, Hsp70 and β-gal ubiquitination was blocked in the presence of CHIPΔTPR. See FIGS. 2B and 6C. scFv13R4-uAbH260Q, which contains an inactivated CHIP domain, was also unable to ubiquinate β-gal. Id. Accordingly, substrate Polyubiquitination was only observed in the presence of an active ubiquibody. In order to confirm the β-gal ubiquitination was cascade dependent, ubiquitination reactions lacking one of the cascade components was performed. See FIG. 3.

Figure 4:
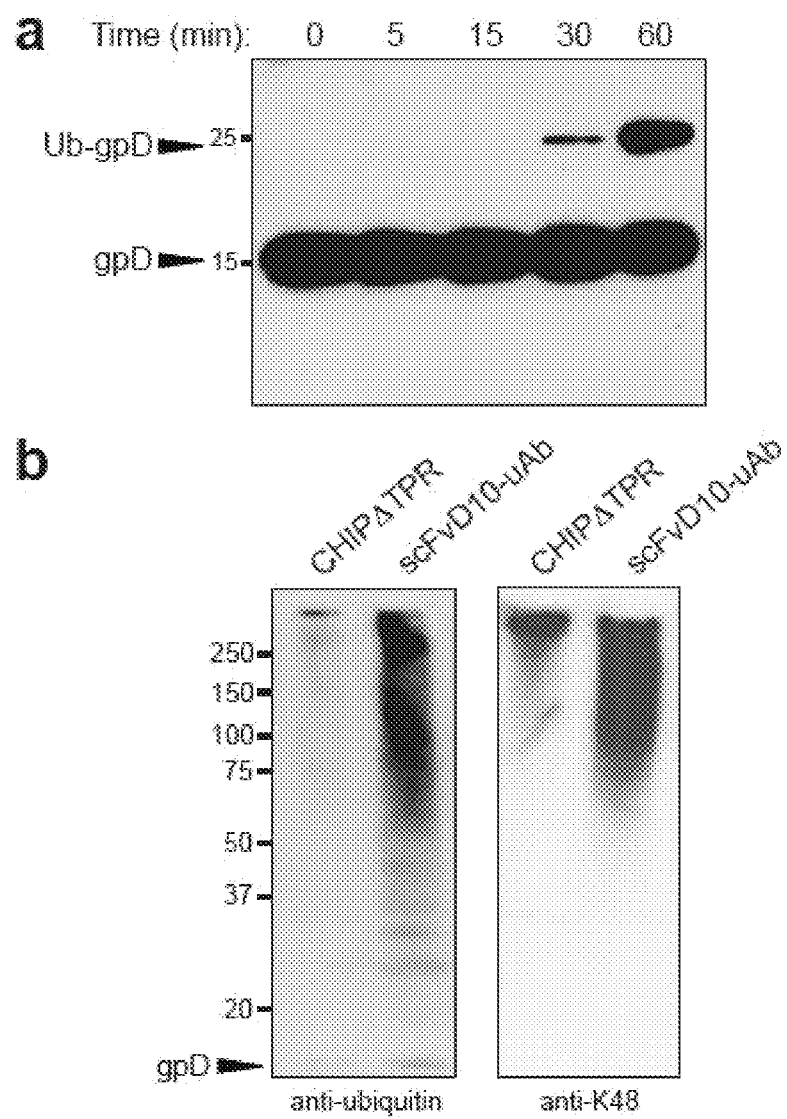
FIGS. 4A-B show the in vitro ubiquitination of gpD.

Ubiquibody modularity, moreover, was assessed by replacing the previously tested scFv domain with scFvD10. The resulting scFvD10-uAb was incubated with gpD (capsid protein D of bacteriophage lambda) and assayed for ubiquitination. See FIGS. 1D and 4A-B. Similar to above, ubiquibody presence is required for Lys48-linked polyubiquitin chain formation. Id.

Figure 5:
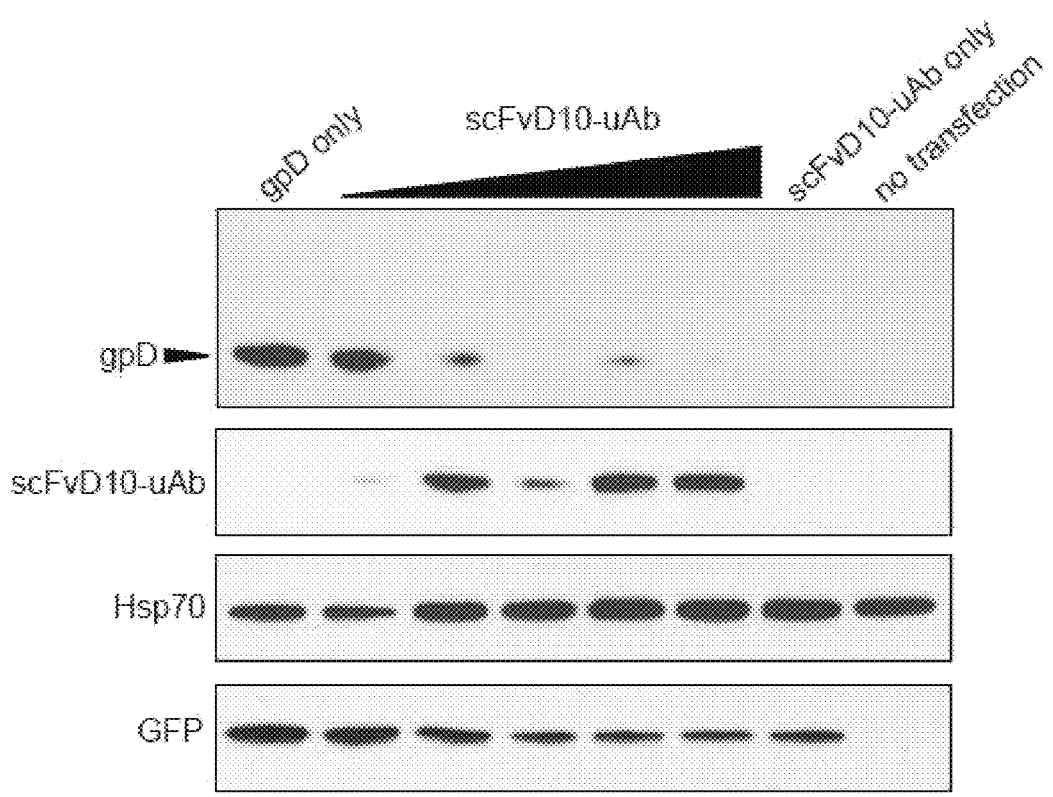
FIG. 5 shows the in vivo ubiquitination and degradation of gpD. Transient transfection of HEK293T cells were performed with increasing amounts of scFvD10-uAb (50 kDa) and a constant concentration of HA-gpD (14.2 kDa). Samples were normalized by total protein for SDS-PAGE and immunobloting analysis with anti-HA and anti-FLAG. Loading controls were detected using anti-Hsp70 (72 kDa) and anti-GFP (27 kDa) antibodies.

In vivo tests were performed using HEK293T cells that were transiently transfected with increasing amounts of scFvD10-uAb in the presence of gpD and GFP. The cells were harvested 48 hours post-transfection and evaluated for the presence of HA-tagged gpD and FLAG-antibody. See FIG. 5. As shown in FIG. 5, the presence of gpD decreases with increasing concentrations of scFvD10-uAb, therefore indicating the ubiquibody-dependent degradation of gpD. Taken together, these results illustrate ubiquibody modularity and functional, in vivo.

Additional or alternative embodiments of the present invention entail the use of different targeting scFvs for protein silencing. Such alternative scFv intrabodies will complement scFv13R4 and scFvD10 intrabodies to target unique substrates. Additional or alternative embodiments will also be employed using different E3 ubiquitin ligases, which may be useful for targeting different tissues, cell types or cellular compartments. Varying linker lengths (and compositions) may provide for increased flexibility, while disparate point mutations in, e.g., the E3 ubiquitin ligase CHIP, may enhance ubiquibody stability.

Additional or alternative approaches in UPS redirection, moreover, include techniques such as, but not limited to, e.g., small synthetic ligands for specified binding ("PROTACs"), fused E3 ligase aptamers, fused antibody fragments to a known degradation target, and chemically induced dimerization products. See Colas et al., "Targeted Modification and Transportation of Cellular Proteins." *Proc Natl Acad Sci USA* 97(25): 13720-5 (2005); Sakamoto et al., "Protacs: Chimeric Molecules that Target Proteins to the Skp1-Cullin-F Box Complex for Ubiquitination and Degradation." *Proc Natl Acad Sci USA* 98(15): 8554-9 (2001); Melchionna et al. (2007). Schneekloth et al., "Targeted Intracellular Protein Degradation Induced by a Small Molecule: En route to Chemical Proteomics." *Bioorg Med Chem Lett* 18(22): 5904-8 (2008); Qian et al. (2009), which are hereby incorporated by reference in their entirety.

The constructs of the present invention, i.e., the chimeric molecules, substrates, and controls, and their concomitant nucleotide and amino acid sequences, are shown below in Table 1.

TABLE 1

Constructs and Sequences

Construct 1:
NcoI-scFvR4-EcoRI-GSGSG-hCHIPdTPR-SalI-FLAGtag-His₆tag-TAA-HindIII
Construct 1 nucleotide sequence:
ATGggcgccgaggtgcagaggtggagtaggggaagcctggtcaagcctgggggtccctgag
actacctgtgcagcctaggattcaccttcagtaactatagcatgaactgggtccgccaggctccaggga
aggggctggagtggatctcatccattagtggtagtagtagatacatactacgcagacttcgtgaagggc
cgattcaccataccagagacaacgccacgaactcactgtacctgcaaatgaacagcctgagagccgag
gacacggctgtttattactgtgtgagatccagtattacgattttggtggcggtatggacgtaggggcagag
gcaccaggtcaccgtacctcaggtggaggcggttcaggcggaggtggcagcggcggtggcggatc
gcagtagtgctgactcagcctgcctccgtgtaggtgtctcctggacagtcgatcaccatctcctgcgctgg
aaccagcagtgacgttggtggttataactatgtacctggtaccaacaacacccaggcaaagcccccaaa
ctcatgatttatgaggacagtaagcggccctcaggggtttctaatcgcttactggaccaagtaggcaac
acggcctccctgacaatactgggctccaggctgaggacgaggctgattattactgcagctcatatacaac
caggagcactcgagttttcggcggagggaccaagaggccgtcctaggtgcggccgcaGAATTC
ggcagcggttctggccggctgaacttcggggacgacatccccagcgctcttcgaatcgcgaagaagaa
gcgctggaacagcattgaggagcggcgcatccaccaggagagcgagctgcactcctacctctccaggc
tcattgccgcggagcgtgagagggagctggaagagtgccagcgaaaccacgagggtgatgaggacga
cagccacgtccgggcccagcaggcctgcattgaggccaagcacgacaagtacatggcggacatggac
gagctttttctcaggtggatgagaagaggaagaagcgagacatccccgactacctgtgtggcaagatca
gattgagctgatgcgggagccgtgcatcacgcccagtggcatcacctacgaccgcaaggacatcgag
gagcacctgcagcgtgtgggtcattttgaccccgtgacccggagcccctgacccaggaacagctcatc
cccaacttggctatgaaggaggttattgacgcattcatctctgagaatggctgggtggaggattacGTC
GACggagcagactacaaggacgatgacgacaagggacatcatcatcatcatcacTAA (SEQ
ID NO: 2).

Construct 1 amino acid sequence:
MGAEVQLVESGGSLVKPGGSLRLSCAASGFTFSNYSMNWVRQAP
GKGLEWISSISGSSRYIYYADFVKGRFTISRDNATNSLYLQMNSLR
AEDTAVYYCVRSSITIFGGGMDVWGRGTLVTVSSGGGGSGGGGS
GGGGSQSVLTQPASVSGSPGQSITISCAGTSSDVGGYNYVSWYQQ
HPGKAPKLMIYEDSKRPSGVSNRFSGSKSGNTASLTISGLQAEDEA
DYYCSSYTTRSTRVFGGGTKLAVLGAAAEFGSGSGRLNFGDDIPS
ALRIAKKKRWNSIEERRIHQESELHSYLSRLIAAERERELEECQRNH
EGDEDDSHVRAQQACIEAKHDKYMADMDELFSQVDEKRKKRDIP
DYLCGKISFELMREPCITPSGITYDRKDIEEHLQRVGHFDPVTRSPL
TQEQLIPNLAMKEVIDAFISENGWVEDYVDGADYKDDDDKGHHH
HHH (SEQ ID NO: 3).

TABLE 1-continued

Constructs and Sequences

Construct 2:
NcoI-scFvgpD-EcoRI-GSGSG-hCHIPdTPR-SalI-FLAGtag-His$_6$tag-TAA-HindIII
Construct 2 nucleotide sequence:
ATGggccttgaagtgcaattggtggaaagcggcggcggcctggtgcaaccgggcggcagcctgcgt
ctgagctgcgcggcctccggatttacctttagcagctatgcgatgagctgggtgcgccaagcccctggga
agggtctcgagtgggtgagcgcgattagcggtagcggcggcagcacctattatgcggatagcgtgaaa
ggccgttttaccatttcacgtgataattcgaaaaacaccctgtatctgcaaatgaacagcctgcgtgcggaa
gatacggccgtgtattattgcgcgcgttttcttatgtttctggtatggattattggggccaaggcaccctggt
gacggttagctcagcgggtggcggttctggcggcggtgggagcggtggcggtggttctggcggtggtg
gttccgatatcgaactgacccagccgccttcagtgagcgttgcaccaggtcagaccgcgcgtatctcgtgt
agcggcgatgcgctgggcgataaatacgcgagctggtaccagcagaaacccgggcaggcgccagttc
tggtgatttatgatgattctgaccgtccctcaggcatcccggaacgctttagcggatccaacagcggcaac
accgcgaccctgaccattagcggcactcaggcggaagacgaagcggattattattgccagagctatgac
aatgatttttatggtactgtgtttggcggcggcacgaagttaaccgttcttggccagGAATTCggcagc
ggttctggccggctgaacttcggggacgacatccccagcgctatcgaatcgcgaagaagaagcgctgg
aacagcattgaggagcggcgcatccaccaggagagcgagctgcactcctacctctccaggctcattgcc
gcggagcgtgagagggagctggaagagtgccagcgaaaccacgagggtgatgaggacgacagcca
cgtccgggcccagcaggcctgcattgaggccaagcacgacaagtacatggcggacatggacgagcttt
tttctcaggtggatgagaagaggaagaagcgagacatccccgactacctgtgtggcaagatcagctttga
gctgatgcgggagccgtgcatcacgcccagtggcatcacctacgaccgcaaggacatcgaggagcac
ctgcagcgtgtgggtcattttgaccccgtgacccggagcccctgacccaggaacagctcatccccaact
tggctatgaaggaggttattgacgcattcatctctgagaatggctgggtggaggattacGTCGACgg
agcagactacaaggacgatgacgacaagggacatcatcatcatcatcacTAA (SEQ ID NO: 4)

Construct 2 amino acid sequence:
MGLEVQLVESGGGLVQPGGSLRLSCAASGFTFSSYAMSWVRQAP
GKGLEWVSAISGSGGSTYYADSVKGRFTISRDNSKNTLYLQMNSL
RAEDTAVYYCARFSYVSGMDYWGQGTLVTVSSAGGGSGGGGSG
GGGSGGGGSDIELTQPPSVSVAPGQTARTSCSGDALGDKYASWYQ
QKPGQAPVLVIYDDSDRPSGIPERFSGSNSGNTATLTISGTQAEDEA
DYYCQSYDNDFYGTVFGGGTKLTVLGQEFGSGSGRLNFGDDIPSA
LRIAKKKRWNSIEERRIHQESELHSYLSRLIAAERERELEECQRNHE
GDEDDSHVRAQQACIEAKHDKYMADMDELFSQVDEKRKKRDIPD
YLCGKISFELMREPCITPSGITYDRKDIEEHLQRVGHFDPVTRSPLT
QEQLIPNLAMKEVIDAFISENGWVEDYVDGADYKDDDDKGHHHH
HH (SEQ ID NO: 5).

Construct 3:
NcoI-hCHIPdTPR-SalI-FLAGtag-His$_6$tag-TAA-HindIII
Construct 3 nucleotide sequence:
ATGggccggctgaacttcggggacgacatccccagcgctatcgaatcgcgaagaagaagcgctgga
acagcattgaggagcggcgcatccaccaggagagcgagctgcactcctacctctccaggctcattgccgc
ggagcgtgagagggagctggaagagtgccagcgaaaccacgagggtgatgaggacgacagccacgtc
cgggcccagcaggcctgcattgaggccaagcacgacaagtacatggcggacatggacgagctttttctc
aggtggatgagaagaggaagaagcgagacatccccgactacctgtgtggcaagatcagattgagctgat
gcgggagccgtgcatcacgcccagtggcatcacctacgaccgcaaggacatcgaggagcacctgcagc
gtgtgggtcattttgaccccgtgacccggagcccctgacccaggaacagctcatccccaacttggctatg
aaggaggttattgacgcattcatctctgagaatggctgggtggaggattacGTCGACggagcagacta
caaggacgatgacgacaagggacatcatcatcatcatcacTAA (SEQ ID NO: 6).

Construct 3 amino acid sequence:
MGRLNFGDDIPSALRIAKKKRWNSIEERRIHQESELHSYLSRLIAAE
RERELEECQRNHEGDEDDSHVRAQQACIEAKHDKYMADMDELFS
QVDEKRKKRDIPDYLCGKISFELMREPCITPSGITYDRKDIEEHLQR
VGHFDPVTRSPLTQEQLIPNLAMKEVIDAFISENGWVEDYVDGAD
YKDDDDKGHHHHHH (SEQ ID NO: 7).

Construct 4:
NcoI-hCHIP-SalI-FLAGtag-His$_6$tag-TAA-HindIII
Construct 4 nucleotide sequence:
ATGggcaagggcaaggaggagaaggagggcggcgcacggctgggcgctggcggcggaagccc
cgagaagagcccgagcgcgcaggagctcaaggagcagggcaatcgtctgttcgtgggccgaaagtac
ccggaggcggcggcctgctacggccgcgcgatcacccggaacccgctggtggccgtgtattacaccaa
ccgggccttgtgctacctgaagatgcagcagcacgagcaggccctggccgactgccggcgcgccctg
gagctggacgggcagtctgtgaaggcgcacttatcctggggcagtgccagctggagatggagactat
gatgaggccatcgccaatctgcagcgagatacagcctggccaaggagcagcggctgaacttcgggga
cgacatccccagcgctatcgaatcgcgaagaagaagcgctggaacagcattgaggagcggcgcatcc
accaggagagcgagctgcactcctacctctccaggctcattgccgcggagcgtgagagggagctggaa
gagtgccagcgaaaccacgagggtgatgaggacgacagccacgtccgggcccagcaggcctgcattg
aggccaagcacgacaagtacatggcggacatggacgagttttctcaggtggatgagaagaggaaga
agcgagacatccccgactacctgtgtggcaagatcagattgagctgatgcgggagccgtgcatcacgc
ccagtggcatcacctacgaccgcaaggacatcgaggagcacctgcagcgtgtgggtcattttgaccccg
tgacccggagcccctgacccaggaacagctcatccccaacttggctatgaaggaggttattgacgcatt
catctctgagaatggctgggtggaggattacGTCGACggagcagactacaaggacgatgacgaca
agggacatcatcatcatcatcacTAA (SEQ ID NO: 8).

TABLE 1-continued

Constructs and Sequences

Construct 4 amino acid sequence:
MGKGKEEKEGGARLGAGGGSPEKSPSAQELKEQGNRLFVGRKYP
EAAACYGRAITRNPLVAVYYTNRALCYLKMQQHEQALADCRRAL
ELDGQSVKAHFFLGQCQLEMESYDEAIANLQRAYSLAKEQRLNFG
DDIPSALRIAKKKRWNSIEERRIHQESELHSYLSRLIAAERERELEEC
QRNHEGDEDDSHVRAQQACIEAKHDKYMADMDELFSQVDEKRK
KRDIPDYLCGKISFELMREPCITPSGITYDRKDIEEHLQRVGHFDPV
TRSPLTQEQLIPNLAMKEVIDAFISENGWVEDYVDGADYKDDDDK
GHHHHHH (SEQ ID NO: 9).

Construct 5:
pET28-NcoI-His$_6$tag-HAtag-NdeI-gpD-TAA-HindIII
Construct 5 nucleotide sequence:
ATGggccatcatcatcatcatcatcactacccgtacgacgttccggactacgctCATATGcttgcgagc
aaagaaacctttacccattaccagccgcagggcaacagtgacccggctcataccgcaaccgcgcccgg
cggattgagtgcgaaagcgcctgcaatgaccccgctgatgctggacacctccagccgtaagctggttgc
gtgggatggcaccaccgacggtgctgccgttggcattcttgcggttgctgctgaccagaccagcaccac
gctgacgttctacaagtccggcacgttccgttatgaggatgtgctctggccggaggctgccagcgacgag
acgaaaaaacggaccgcgtttgccggaacggcaatcagcatcgttTAA (SEQ ID NO: 10).

Construct 5 amino acid sequence:
MGHHHHHHYPYDVPDYAHMLASKETFTHYQPQGNSDPAHTATA
PGGLSAKAPAMTPLMLDTSSRKLVAWDGTTDGAAVGILAVAADQ
TSTTLTFYKSGTFRYEDVLWPEAASDETKKRTAFAGTAISIV (SEQ
ID NO: 11).

Construct 6:
pCDNA3:HindIII-Kozak-scEvR4-EcoRI-GSGSG-hCHIPdTPR-SalI-FLAGtag-His$_6$tag-
TAA-XbaI
Construct 6 nucleotide sequence:
ATGgccgaggtgcagctggtggagtctgggggaagcctggtcaagcctggggggtccctgagactc
tcctgtgcagcctctggattcaccttcagtaactatagcatgaactgggtccgccaggctccagggaaggg
gctggagtggatctcatccattagtggtagtagtagatacatatactacgcagacttcgtgaagggccgatt
caccatctccagagacaacgccacgaactcactgtacctgcaaatgaacagcctgagagccgaggaca
cggctgtttattactgtgtgagatccagtattacgattttttggtggcgtctggggcagaggcac
cctggtcaccgtctcctcaggtggaggcggttcaggcggaggtggcagcggcggtggcggatcgcagt
ctgtgctgactcagcctgcctccgtgtctgggtctcctggacagtcgatcaccatctcctgcgctggaacca
gcagtgacgttggtggttataactatgtctcctggtaccaacaacacccaggcaaagcccccaaactcatg
atttatgaggacagtaagcggccctcaggggtttctaatcgcttctctggctccaagtctggcaacacggc
ctccctgacaatctctgggctccaggctgaggacgaggctgattattactgcagctcatatacaaccagga
gcactcgagttttcggcggagggaccaagctggccgtcctaggtgcggccgcaGAATTCggcag
cggttctggccggctgaacttcggggacgacatccccagcgctatcgaatcgcgaagaagaagcgctg
gaacagcattgaggagcggcgcatccaccaggagagcgagctgcactcctacctctccaggctcattgc
cgcggagcgtgagagggagctggaagagtgccagcgaaaccacgagggtgatgaggacgacagcc
acgtccgggcccagcaggcctgcattgaggccaagcacgacaagtacatggcggacatggacgagctt
ttttctcaggtggatgagaagaggaagaagcgagacatccccgactacctgtgtggcaagatcagctttg
agctgatgcgggagccgtgcatcacgcccagtggcatcacctacgaccgcaaggacatgaggagca
cctgcagcgtgtgggtcattttgaccccgtgacccggagccccctgacccaggaacagctcatcccaa
cttggctatgaaggaggttattgacgcattcatctctgagaatggctgggtggaggattacGTCGACg
gagcagactacaaggacgatgacgacaagggacatcatcatcatcatcacTAA (SEQ ID NO:
12).

Construct 6 amino acid sequence:
MAEVQLVESGGSLVKPGGSLRLSCAASGFTFSNYSMNWVRQAPG
KGLEWISSISGSSRYIYYADFVKGRFTISRDNATNSLYLQMNSLRA
EDTAVYYCVRSSITIFGGGMDVWGRGTLVTVSSGGGGSGGGGSG
GGGSQSVLTQPASVSGSPGQSITISCAGTSSDVGGYNYVSWYQQH
PGKAPKLMIYEDSKRPSGVSNRFSGSKSGNTASLTISGLQAEDEAD
YYCSSYTTRSTRVFGGGTKLAVLGAAAEFGSGSGRLNFGDDIPSAL
RIAKKKRWNSIEERRIHQESELHSYLSRLIAAERERELEECQRNHEG
DEDDSHVRAQQACIEAKHDKYMADMDELFSQVDEKRKKRDIPDY
LCGKISFELMREPCITPSGITYDRKDIEEHLQRVGHFDPVTRSPLTQ
EQLIPNLAMKEVIDAFISENGWVEDYVDGADYKDDDDKGHHHHH
H (SEQ ID NO: 13).

Construct 7:
pCDNA3:HindIII-Kozak-scFvgpD-EcoRI-GSGSG-hCHIPdTPR-SalI-FLAGtag-His$_6$tag-
TAA-XbaI
Construct 7 nucleotide sequence:
ATGgcccttgaagtgcaattggtggaaagcggcggcggcctggtgcaacggggcggcagcctgcgt
ctgagctgcgcggcctccggattacctttagcagctatgcgatgagctgggtgcgccaagcccctggga
agggtctcgagtgggtgagcgcgattagcggtagcggcggcagcaccctattatgcggatagcgtgaaa
ggccgttttaccatttcacgtgataattctgaaaaacaccctgtatctgcaaatgaacagcctgcgtgcggaa
gatacggccgtgtattattgcgcgcgttttcttatgtttctggtatggattattgggccaaggcaccctggt
gacggttagctcagcgggtggcggttctggcggcggtgggagcggtggcggtggttctggcggtggtg
gttccgatatcgaactgacccagccgcctcagtgagcgttgcaccaggtcagaccgcgcgtatctcgtgt
agcggcgatgcgctgggcgataaatacgcgagctggtaccagcagaaacccgggcaggcgccagttc TABLE 1-continued Constructs and Sequences tggtgatttatgatgattctgaccgtccctcaggcatcccggaacgctttagcggatccaacagcggcaac
accgcgaccctgaccattagcggcactcaggcggaagacgaagcggattattattgccagagctatgac
aatgattttatggtactgtgtttggcggcggcacgaagttaaccgttcttggccagGAATTCggcagc
ggttctggccggctgaacttcggggacgacatccccagcgctatcgaatcgcgaagaagaagcgctgg
aacagcattgaggagcggcgcatccaccaggagagcgagctgcactcctacctctccaggctcattgcc
gcggagcgtgagagggagctggaagagtgccagcgaaaccacgagggtgatgaggacgacagcca
cgtccgggcccagcaggcctgcattgaggccaagcacgacaagtacatggcggacatggacgagcttt
tttctcaggtggatgagaagaggaagaagcgagacatccccgactacctgtgtggcaagatcagctttga
gctgatgcgggagccgtgcatcacgcccagtggcatcacctacgaccgcaaggacatcgaggagcac
ctgcagcgtgtgggtcattttgaccccgtgacccggagcccctgacccaggaacagctcatccccaact
tggctatgaaggaggttattgacgcattcatctctgagaatggctgggtggaggattacGTCGACgg
agcagactacaaggacgatgacgacaagggacatcatcatcatcatcacTAA (SEQ ID NO: 14).

Construct 7 amino acid sequence:
MALEVQLVESGGGLVQPGGSLRLSCAASGFTFSSYAMSWVRQAP
GKGLEWVSAISGSGGSTYYADSVKGRFTISRDNSKNTLYLQMNSL
RAEDTAVYYCARFSYVSGMDYWGQGTLVTVSSAGGGSGGGGSG
GGGSGGGGSDIELTQPPSVSVAPGQTARTSCSGDALGDKYASWYQ
QKPGQAPVLVIYDDSDRPSGIPERFSGSNSGNTATLTISGTQAEDEA
DYYCQSYDNDFYGTVFGGGTKLTVLGQEFGSGSGRLNFGDDIPSA
LRIAKKKRWNSIEERRIHQESELHSYLSRLIAAERERELEECQRNHE
GDEDDSHVRAQQACIEAKHDKYMADMDELFSQVDEKRKKRDIPD
YLCGKISFELMREPCITPSGITYDRKDIEEHLQRVGHFDPVTRSPLT
QEQLIPNLAMKEVIDAFISENGWVEDYVDGADYKDDDDKGHHHH
HH (SEQ ID NO: 15).

Construct 8:
pCMV-HA-gpD:NotI-HA-NdeI-gpD-TAA-NotI
Construct 8 nucleotide sequence:
ATGtacccgtacgacgttccggactacgctCATATGatgcgagcaaagaaacctttacccattac
cagccgcagggcaacagtgacccggctcataccgcaaccgcgcccggcggattgagtgcgaaagcgc
ctgcaatgaccccgctgatgctggacacctccagccgtaagaggttgcgtgggatggcaccaccgacg
gtgctgccgttggcattcttgcggttgctgctgaccagaccagcaccacgctgacgttctacaagtccggc
acgttccgttatgaggatgtgactggccggaggctgccagcgacgagacgaaaaaacggaccgcgttt
gccggaacggcaatcagcatcgttTAA (SEQ ID NO: 16).

Construct 8 amino acid sequence:
MYPYDVPDYAHMLASKETFTHYQPQGNSDPAHTATAPGGLSAKA
PAMTPLMLDTSSRKLVAWDGTTDGAAVGILAVAADQTSTTLTFY
KSGTFRYEDVLWPEAASDETKKRTAFAGTAISIV (SEQ ID NO: 17).

Although preferred embodiments have been depicted and described in detail herein, it will be apparent to those skilled in the relevant art that various modifications, additions, substitutions, and the like can be made without departing from the spirit of the invention. These are therefore considered to be within the scope of the invention as defined in the claims which follow.

What is claimed:

1. An isolated chimeric molecule comprising:
   a degradation domain comprising a eukaryotic U-box motif of an E3 ligase, wherein the U-box motif is a carboxyl terminus of human Hsc70-Interacting Protein ("CHIP (STUB1)"), wherein the chimeric molecule does not comprise the E3 ligase's N-terminal tetratricopeptide repeat ("TPR") domain;
   a targeting domain directing said degradation domain to an intracellular substrate, wherein said targeting domain is an antibody or an antigen binding fragment thereof, said targeting domain being heterologous to said degradation domain; and
   a linker coupling said degradation domain to said targeting domain, wherein said linker domain is heterologous to said degradation domain and heterologous to said targeting domain.

2. The chimeric molecule of claim 1, wherein said degradation domain lacks an endogenous substrate recognition region.

3. The chimeric molecule of claim 1, wherein said U-box motif permits proteolysis of said intracellular substrate.

4. The chimeric molecule of claim 1, wherein said U-box motif possesses a cell-type specific or tissue specific ligase function.

5. The chimeric molecule of claim 4, wherein said ligase function is cell-type specific and the cell-type is selected from the group consisting of muscle cells, airway cells, microvascular cells, placental cells, hepatocytes, glial cells, kidney cells, pancreatic islets, and neuroblasts.

6. The chimeric molecule of claim 1, wherein said targeting domain binds said intracellular substrate.

7. The chimeric molecule of claim 1, wherein said targeting domain is a polyclonal antibody, a monoclonal antibody, a recombinant antibody, a Fab', a F(ab')$_2$, a Fv, a scFv, a tascFvs, a bis-scFvs, a sdAb, a V$_{nar}$, a scFvD10 that bind to capsid protein D (gpD), a scFv13R4 that binds to beta-galactosidase, a humanized antibody, a chimeric antibody, a IgA antibody, a IgD antibody, a IgE antibody, a IgG antibody, a IgM antibody, a nanobody, a intrabody, a unibody, or a minibody.

8. The chimeric molecule of claim 1, wherein said linker is a polypeptide linker of sufficient length to prevent the steric disruption of binding between said targeting domain and said intracellular substrate.

9. The chimeric molecule of claim 1, wherein said linker is not cleavable.

10. The chimeric molecule of claim 1, wherein said linker is enzymatically or hydrolytically cleavable.

11. A composition comprising:
the chimeric molecule of claim 1; and
a pharmaceutically-acceptable carrier.

12. The composition of claim 11 further comprising:
a second agent selected from the group consisting of an anti-inflammatory agent, an antidiabetic agent, a hypolipidemic agent, a chemotherapeutic agent, an antiviral agent, an antibiotic, a metabolic agent, a small molecule inhibitor, a protein kinase inhibitor, an adjuvant, an apoptotic agent, a proliferative agent, an organotropic targeting agent, and a combination thereof.

13. The chimeric molecule of claim 1, wherein the linker is a glycine-serine linker.

14. The chimeric molecule of claim 13, wherein the linker comprises the amino acid sequence of SEQ ID NO: 1.

* * * * *

SEQUENCE LISTING

<160> NUMBER OF SEQ ID NOS: 17

<210> SEQ ID NO 1
<211> LENGTH: 5
<212> TYPE: PRT
<213> ORGANISM: Artificial
<220> FEATURE:
<223> OTHER INFORMATION: Linker

<400> SEQUENCE: 1

Gly Ser Gly Ser Gly
1               5

<210> SEQ ID NO 2
<211> LENGTH: 1368
<212> TYPE: DNA
<213> ORGANISM: Artificial
<220> FEATURE:

<223> OTHER INFORMATION: Construct 1 Nucleotide Sequence

<400> SEQUENCE: 2

```
atgggcgccg aggtgcagct ggtggagtct gggggaagcc tggtcaagcc tgggggtcc    60
ctgagactct cctgtgcagc ctctggattc accttcagta actatagcat gaactgggtc   120
cgccaggctc cagggaaggg gctggagtgg atctcatcca ttagtggtag tagtagatac   180
atatactacg cagacttcgt gaagggccga ttcaccatct ccagagacaa cgccacgaac   240
tcactgtacc tgcaaatgaa cagcctgaga gccgaggaca cggctgttta ttactgtgtg   300
agatccagta ttacgatttt tggtggcggt atggacgtct ggggcagagg caccctggtc   360
accgtctcct caggtggagg cggttcaggc ggaggtggca gcggcggtgg cggatcgcag   420
tctgtgctga ctcagcctgc ctccgtgtct gggtctcctg gacagtcgat caccatctcc   480
tgcgctggaa ccagcagtga cgttggtggt tataactatg tctcctggta ccaacaacac   540
ccaggcaaag cccccaaact catgatttat gaggacagta gcggccctc agggggtttct   600
aatcgcttct ctggctccaa gtctggcaac acggcctccc tgacaatctc tgggctccag   660
gctgaggacg aggctgatta ttactgcagc tcatatacaa ccaggagcac tcgagttttc   720
ggcggaggga ccaagctggc cgtcctaggt gcggccgcag aattcggcag cggttctggc   780
cggctgaact cggggacga catccccagc gctcttcgaa tcgcgaagaa gaagcgctgg   840
aacagcattg aggagcggcg catccaccag gagagcgagc tgcactccta cctctccagg   900
ctcattgccg cggagcgtga gggagctg aagagtgcc agcgaaacca cgagggtgat   960
gaggacgaca gccacgtccg ggcccagcag gcctgcattg aggccaagca cgacaagtac  1020
atggcggaca tggacgagct tttttctcag gtggatgaga agaggaagaa gcgagacatc  1080
cccgactacc tgtgtggcaa gatcagcttt gagctgatgc gggagccgtg catcacgccc  1140
agtggcatca cctacgaccg caaggacatc gaggagcacc tgcagcgtgt gggtcatttt  1200
gaccccgtga cccggagccc cctgacccag gaacagctca tccccaactt ggctatgaag  1260
gaggttattg acgcattcat ctctgagaat ggctgggtgg aggattacgt cgacggagca  1320
gactacaagg acgatgacga caagggacat catcatcatc atcactaa              1368
```

<210> SEQ ID NO 3
<211> LENGTH: 455
<212> TYPE: PRT
<213> ORGANISM: Artificial
<220> FEATURE:
<223> OTHER INFORMATION: Construct 1 Amino Acid Sequence

<400> SEQUENCE: 3

Met Gly Ala Glu Val Gln Leu Val Glu Ser Gly Gly Ser Leu Val Lys
1               5                   10                  15

Pro Gly Gly Ser Leu Arg Leu Ser Cys Ala Ala Ser Gly Phe Thr Phe
            20                  25                  30

Ser Asn Tyr Ser Met Asn Trp Val Arg Gln Ala Pro Gly Lys Gly Leu
        35                  40                  45

Glu Trp Ile Ser Ser Ile Ser Gly Ser Ser Arg Tyr Ile Tyr Tyr Ala
    50                  55                  60

Asp Phe Val Lys Gly Arg Phe Thr Ile Ser Arg Asp Asn Ala Thr Asn
65                  70                  75                  80

Ser Leu Tyr Leu Gln Met Asn Ser Leu Arg Ala Glu Asp Thr Ala Val
                85                  90                  95

Tyr Tyr Cys Val Arg Ser Ser Ile Thr Ile Phe Gly Gly Gly Met Asp

```
              100                 105                 110
Val Trp Gly Arg Gly Thr Leu Val Thr Val Ser Ser Gly Gly Gly
            115                 120                 125
Ser Gly Gly Gly Gly Ser Gly Gly Gly Ser Gln Ser Val Leu Thr
            130                 135                 140
Gln Pro Ala Ser Val Ser Gly Ser Pro Gly Gln Ser Ile Thr Ile Ser
145                 150                 155                 160
Cys Ala Gly Thr Ser Ser Asp Val Gly Gly Tyr Asn Tyr Val Ser Trp
            165                 170                 175
Tyr Gln Gln His Pro Gly Lys Ala Pro Lys Leu Met Ile Tyr Glu Asp
            180                 185                 190
Ser Lys Arg Pro Ser Gly Val Ser Asn Arg Phe Ser Gly Ser Lys Ser
            195                 200                 205
Gly Asn Thr Ala Ser Leu Thr Ile Ser Gly Leu Gln Ala Glu Asp Glu
            210                 215                 220
Ala Asp Tyr Tyr Cys Ser Ser Tyr Thr Thr Arg Ser Thr Arg Val Phe
225                 230                 235                 240
Gly Gly Gly Thr Lys Leu Ala Val Leu Gly Ala Ala Ala Glu Phe Gly
            245                 250                 255
Ser Gly Ser Gly Arg Leu Asn Phe Gly Asp Asp Ile Pro Ser Ala Leu
            260                 265                 270
Arg Ile Ala Lys Lys Lys Arg Trp Asn Ser Ile Glu Glu Arg Arg Ile
            275                 280                 285
His Gln Glu Ser Glu Leu His Ser Tyr Leu Ser Arg Leu Ile Ala Ala
            290                 295                 300
Glu Arg Glu Arg Glu Leu Glu Glu Cys Gln Arg Asn His Glu Gly Asp
305                 310                 315                 320
Glu Asp Asp Ser His Val Arg Ala Gln Gln Ala Cys Ile Glu Ala Lys
            325                 330                 335
His Asp Lys Tyr Met Ala Asp Met Asp Glu Leu Phe Ser Gln Val Asp
            340                 345                 350
Glu Lys Arg Lys Lys Arg Asp Ile Pro Asp Tyr Leu Cys Gly Lys Ile
            355                 360                 365
Ser Phe Glu Leu Met Arg Glu Pro Cys Ile Thr Pro Ser Gly Ile Thr
            370                 375                 380
Tyr Asp Arg Lys Asp Ile Glu Glu His Leu Gln Arg Val Gly His Phe
385                 390                 395                 400
Asp Pro Val Thr Arg Ser Pro Leu Thr Gln Glu Gln Leu Ile Pro Asn
            405                 410                 415
Leu Ala Met Lys Glu Val Ile Asp Ala Phe Ile Ser Glu Asn Gly Trp
            420                 425                 430
Val Glu Asp Tyr Val Asp Gly Ala Asp Tyr Lys Asp Asp Asp Lys
            435                 440                 445
Gly His His His His His
    450                 455

<210> SEQ ID NO 4
<211> LENGTH: 1362
<212> TYPE: DNA
<213> ORGANISM: Artificial
<220> FEATURE:
<223> OTHER INFORMATION: Construct 2 Nucleotide Sequence

<400> SEQUENCE: 4
atgggccttg aagtgcaatt ggtggaaagc ggcggcggcc tggtgcaacc gggcggcagc    60
```

-continued

```
ctgcgtctga gctgcgcggc ctccggattt acctttagca gctatgcgat gagctgggtg      120
cgccaagccc ctgggaaggg tctcgagtgg gtgagcgcga ttagcggtag cggcggcagc      180
acctattatg cggatagcgt gaaaggccgt tttaccattt cacgtgataa ttcgaaaaac      240
accctgtatc tgcaaatgaa cagcctgcgt gcggaagata cggccgtgta ttattgcgcg      300
cgttttcctt atgtttctgg tatggattat tggggccaag caccctggt gacggttagc       360 tcagcgggtg gcggttctgg cggcggtggg agcggtggcg gtggttctgg cggtggtggt      420
tccgatatcg aactgaccca gccgccttca gtgagcgttg caccaggtca gaccgcgcgt      480
atctcgtgta gcggcgatgc gctgggcgat aaatacgcga gctggtacca gcagaaaccc      540
gggcaggcgc cagttctggt gatttatgat gattctgacc gtccctcagg catcccggaa      600
cgctttagcg gatccaacag cggcaacacc gcgaccctga ccattagcgg cactcaggcg      660
gaagacgaag cggattatta ttgccagagc tatgacaatg attttatgg tactgtgttt       720 ggcggcggca cgaagttaac cgttcttggc caggaattcg gcagcggttc tggccggctg      780
aacttcgggg acgacatccc cagcgctctt cgaatcgcga agaagaagcg ctggaacagc      840
attgaggagc ggcgcatcca ccaggagagc gagctgcact cctacctctc caggctcatt      900
gccgcggagc gtgagaggga gctggaagag tgccagcgaa ccacgagggg tgatgaggac      960
gacagccacg tccgggccca gcaggcctgc attgaggcca gcacgacaa gtacatggcg      1020 gacatggacg agctttttc tcaggtggat gagaagagga agaagcgaga catccccgac       1080
tacctgtgtg caagatcag ctttgagctg atgcgggagc cgtgcatcac gcccagtggc       1140
atcacctacg accgcaagga catcgaggag cacctgcagc gtgtgggtca ttttgacccc      1200
gtgacccgga gccccctgac ccaggaacag ctcatcccca acttggctat gaaggaggtt      1260
attgacgcat tcatctctga aatggctgg gtggaggatt acgtcgacgg agcagactac       1320
aaggacgatg acgacaaggg acatcatcat catcatcact aa                        1362
```

<210> SEQ ID NO 5
<211> LENGTH: 453
<212> TYPE: PRT
<213> ORGANISM: Artificial
<220> FEATURE:
<223> OTHER INFORMATION: Construct 2 Amino Acid Sequence

<400> SEQUENCE: 5

```
Met Gly Leu Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Phe Ser Tyr Val Ser Gly Met Asp Tyr Trp Gly
            100                 105                 110

Gln Gly Thr Leu Val Thr Val Ser Ser Ala Gly Gly Ser Gly Gly
        115                 120                 125
```

Gly Gly Ser Gly Gly Gly Ser Gly Gly Gly Ser Asp Ile Glu
    130             135             140

Leu Thr Gln Pro Pro Ser Val Ser Val Ala Pro Gly Gln Thr Ala Arg
145                 150                 155                 160

Ile Ser Cys Ser Gly Asp Ala Leu Gly Asp Lys Tyr Ala Ser Trp Tyr
                165                 170                 175

Gln Gln Lys Pro Gly Gln Ala Pro Val Leu Val Ile Tyr Asp Asp Ser
            180                 185                 190

Asp Arg Pro Ser Gly Ile Pro Glu Arg Phe Ser Gly Ser Asn Ser Gly
        195                 200                 205

Asn Thr Ala Thr Leu Thr Ile Ser Gly Thr Gln Ala Glu Asp Glu Ala
    210                 215                 220

Asp Tyr Tyr Cys Gln Ser Tyr Asp Asn Asp Phe Tyr Gly Thr Val Phe
225                 230                 235                 240

Gly Gly Gly Thr Lys Leu Thr Val Leu Gly Gln Glu Phe Gly Ser Gly
                245                 250                 255

Ser Gly Arg Leu Asn Phe Gly Asp Asp Ile Pro Ser Ala Leu Arg Ile
                260                 265                 270

Ala Lys Lys Lys Arg Trp Asn Ser Ile Glu Glu Arg Ile His Gln
    275                 280                 285

Glu Ser Glu Leu His Ser Tyr Leu Ser Arg Leu Ile Ala Ala Glu Arg
    290                 295                 300

Glu Arg Glu Leu Glu Glu Cys Gln Arg Asn His Glu Gly Asp Glu Asp
305                 310                 315                 320

Asp Ser His Val Arg Ala Gln Gln Ala Cys Ile Glu Ala Lys His Asp
                325                 330                 335

Lys Tyr Met Ala Asp Met Asp Glu Leu Phe Ser Gln Val Asp Glu Lys
                340                 345                 350

Arg Lys Lys Arg Asp Ile Pro Asp Tyr Leu Cys Gly Lys Ile Ser Phe
            355                 360                 365

Glu Leu Met Arg Glu Pro Cys Ile Thr Pro Ser Gly Ile Thr Tyr Asp
        370                 375                 380

Arg Lys Asp Ile Glu Glu His Leu Gln Arg Val Gly His Phe Asp Pro
385                 390                 395                 400

Val Thr Arg Ser Pro Leu Thr Gln Glu Gln Leu Ile Pro Asn Leu Ala
                405                 410                 415

Met Lys Glu Val Ile Asp Ala Phe Ile Ser Glu Asn Gly Trp Val Glu
                420                 425                 430

Asp Tyr Val Asp Gly Ala Asp Tyr Lys Asp Asp Asp Lys Gly His
            435                 440                 445

His His His His His
    450

<210> SEQ ID NO 6
<211> LENGTH: 594
<212> TYPE: DNA
<213> ORGANISM: Artificial
<220> FEATURE:
<223> OTHER INFORMATION: Construct 3 Nucleotide Sequence

<400> SEQUENCE: 6
atgggccggc tgaacttcgg ggacgacatc cccagcgctc ttcgaatcgc gaagaagaag    60
cgctggaaca gcattgagga gcggcgcatc caccaggaga gcgagctgca ctcctacctc   120
tccaggctca ttgccgcgga gcgtgagagg gagctggaag agtgccagcg aaaccacgag   180

```
ggtgatgagg acgacagcca cgtccgggcc cagcaggcct gcattgaggc caagcacgac      240
aagtacatgg cggacatgga cgagcttttt tctcaggtgg atgagaagag gaagaagcga      300
gacatccccg actacctgtg tggcaagatc agctttgagc tgatgcggga gccgtgcatc      360
acgcccagtg gcatcaccta cgaccgcaag gacatcgagg agcacctgca gcgtgtgggt      420
cattttgacc ccgtgacccg gagccccctg acccaggaac agctcatccc caacttggct      480
atgaaggagg ttattgacgc attcatctct gagaatggct gggtggagga ttacgtcgac      540
ggagcagact acaaggacga tgacgacaag ggacatcatc atcatcatca ctaa            594
```

<210> SEQ ID NO 7
<211> LENGTH: 197
<212> TYPE: PRT
<213> ORGANISM: Artificial
<220> FEATURE:
<223> OTHER INFORMATION: Construct 3 Amino Acid Sequence

<400> SEQUENCE: 7

```
Met Gly Arg Leu Asn Phe Gly Asp Asp Ile Pro Ser Ala Leu Arg Ile
1               5                   10                  15

Ala Lys Lys Arg Trp Asn Ser Ile Glu Glu Arg Ile His Gln
            20                  25                  30

Glu Ser Glu Leu His Ser Tyr Leu Ser Arg Leu Ile Ala Ala Glu Arg
        35                  40                  45

Glu Arg Glu Leu Glu Glu Cys Gln Arg Asn His Gly Asp Glu Asp
    50                  55                  60

Asp Ser His Val Arg Ala Gln Gln Ala Cys Ile Glu Ala Lys His Asp
65                  70                  75                  80

Lys Tyr Met Ala Asp Met Asp Glu Leu Phe Ser Gln Val Asp Glu Lys
                85                  90                  95

Arg Lys Lys Arg Asp Ile Pro Asp Tyr Leu Cys Gly Lys Ile Ser Phe
            100                 105                 110

Glu Leu Met Arg Glu Pro Cys Ile Thr Pro Ser Gly Ile Thr Tyr Asp
        115                 120                 125

Arg Lys Asp Ile Glu Glu His Leu Gln Arg Val Gly His Phe Asp Pro
    130                 135                 140

Val Thr Arg Ser Pro Leu Thr Gln Glu Gln Leu Ile Pro Asn Leu Ala
145                 150                 155                 160

Met Lys Glu Val Ile Asp Ala Phe Ile Ser Glu Asn Gly Trp Val Glu
                165                 170                 175

Asp Tyr Val Asp Gly Ala Asp Tyr Lys Asp Asp Asp Lys Gly His
            180                 185                 190

His His His His
        195
```

<210> SEQ ID NO 8
<211> LENGTH: 972
<212> TYPE: DNA
<213> ORGANISM: Artificial
<220> FEATURE:
<223> OTHER INFORMATION: Construct 4 Nucleotide Sequence

<400> SEQUENCE: 8

```
atgggcaagg gcaaggagga aggagggc ggcgcacggc tgggcgctgg cggcggaagc       60
cccgagaaga gcccgagcgc gcaggagctc aaggagcagg caatcgtct gttcgtgggc      120 cgaaagtacc cggaggcggc ggcctgctac ggccgcgcga tcacccggaa cccgctggtg     180
```

```
gccgtgtatt acaccaaccg ggccttgtgc tacctgaaga tgcagcagca cgagcaggcc    240
ctggccgact gccggcgcgc cctggagctg gacgggcagt ctgtgaaggc gcacttcttc    300
ctggggcagt gccagctgga gatggagagc tatgatgagg ccatcgccaa tctgcagcga    360
gcttacagcc tggccaagga gcagcggctg aacttcgggg acgacatccc cagcgctctt    420
cgaatcgcga agaagaagcg ctggaacagc attgaggagc ggcgcatcca ccaggagagc    480
gagctgcact cctacctctc caggctcatt gccgcggagc gtgagggga gctgaagag     540
tgccagcgaa accacgaggg tgatgaggac acagccacg tccgggccca gcaggcctgc    600
attgaggcca gcacgacaa gtacatggcg gacatggacg agcttttttc tcaggtggat    660
gagaagagga agaagcgaga catccccgac tacctgtgtg caagatcag ctttgagctg    720
atgcgggagc cgtgcatcac gcccagtggc atcacctacg accgcaagga catcgaggag    780
cacctgcagc gtgtgggtca ttttgacccc gtgacccgga gcccctgac ccaggaacag    840
ctcatcccca acttggctat gaaggaggtt attgacgcat tcatctctga gaatggctgg    900
gtggaggatt acgtcgacgg agcagactac aaggacgatg acgacaaggg acatcatcat    960
catcatcact aa                                                       972
```

```
<210> SEQ ID NO 9
<211> LENGTH: 323
<212> TYPE: PRT
<213> ORGANISM: Artificial
<220> FEATURE:
<223> OTHER INFORMATION: Construct 4 Amino Acid Sequence

<400> SEQUENCE: 9
```

Met Gly Lys Gly Lys Glu Glu Lys Glu Gly Gly Ala Arg Leu Gly Ala
1               5                   10                  15

Gly Gly Gly Ser Pro Glu Lys Ser Pro Ser Ala Gln Glu Leu Lys Glu
            20                  25                  30

Gln Gly Asn Arg Leu Phe Val Gly Arg Lys Tyr Pro Glu Ala Ala Ala
        35                  40                  45

Cys Tyr Gly Arg Ala Ile Thr Arg Asn Pro Leu Val Ala Val Tyr Tyr
    50                  55                  60

Thr Asn Arg Ala Leu Cys Tyr Leu Lys Met Gln His Glu Gln Ala
65                  70                  75                  80

Leu Ala Asp Cys Arg Arg Ala Leu Glu Leu Asp Gly Gln Ser Val Lys
                85                  90                  95

Ala His Phe Phe Leu Gly Gln Cys Gln Leu Glu Met Glu Ser Tyr Asp
            100                 105                 110

Glu Ala Ile Ala Asn Leu Gln Arg Ala Tyr Ser Leu Ala Lys Glu Gln
        115                 120                 125

Arg Leu Asn Phe Gly Asp Asp Ile Pro Ser Ala Leu Arg Ile Ala Lys
    130                 135                 140

Lys Lys Arg Trp Asn Ser Ile Glu Glu Arg Arg Ile His Gln Glu Ser
145                 150                 155                 160

Glu Leu His Ser Tyr Leu Ser Arg Leu Ile Ala Ala Glu Arg Glu Arg
                165                 170                 175

Glu Leu Glu Glu Cys Gln Arg Asn His Glu Gly Asp Glu Asp Ser
            180                 185                 190

His Val Arg Ala Gln Gln Ala Cys Ile Glu Ala Lys His Asp Lys Tyr
        195                 200                 205

Met Ala Asp Met Asp Glu Leu Phe Ser Gln Val Asp Glu Lys Arg Lys
    210                 215                 220

```
Lys Arg Asp Ile Pro Asp Tyr Leu Cys Gly Lys Ile Ser Phe Glu Leu
225                 230                 235                 240

Met Arg Glu Pro Cys Ile Thr Pro Ser Gly Ile Thr Tyr Asp Arg Lys
                245                 250                 255

Asp Ile Glu Glu His Leu Gln Arg Val Gly His Phe Asp Pro Val Thr
            260                 265                 270

Arg Ser Pro Leu Thr Gln Glu Gln Leu Ile Pro Asn Leu Ala Met Lys
        275                 280                 285

Glu Val Ile Asp Ala Phe Ile Ser Glu Asn Gly Trp Val Glu Asp Tyr
    290                 295                 300

Val Asp Gly Ala Asp Tyr Lys Asp Asp Asp Lys Gly His His His
305                 310                 315                 320

His His His

<210> SEQ ID NO 10
<211> LENGTH: 390
<212> TYPE: DNA
<213> ORGANISM: Artificial
<220> FEATURE:
<223> OTHER INFORMATION: Construct 5 Nucleotide Sequence

<400> SEQUENCE: 10
atgggccatc atcatcatca tcactacccg tacgacgttc cggactacgc tcatatgctt      60
gcgagcaaag aaacctttac ccattaccag ccgcagggca acagtgaccc ggctcatacc     120
gcaaccgcgc ccggcggatt gagtgcgaaa gcgcctgcaa tgacccccgct gatgctggac     180 acctccagcc gtaagctggt tgcgtgggat ggcaccaccg acggtgctgc cgttggcatt     240
cttgcggttg ctgctgacca gaccagcacc acgctgacgt tctacaagtc cggcacgttc     300
cgttatgagg atgtgctctg gccggaggct gccagcgacg agacgaaaaa acggaccgcg     360
tttgccggaa cggcaatcag catcgtttaa                                      390

<210> SEQ ID NO 11
<211> LENGTH: 129
<212> TYPE: PRT
<213> ORGANISM: Artificial
<220> FEATURE:
<223> OTHER INFORMATION: Construct 5 Amino Acid Sequence

<400> SEQUENCE: 11

Met Gly His His His His His His Tyr Pro Tyr Asp Val Pro Asp Tyr
1               5                   10                  15

Ala His Met Leu Ala Ser Lys Glu Thr Phe Thr His Tyr Gln Pro Gln
            20                  25                  30

Gly Asn Ser Asp Pro Ala His Thr Ala Thr Ala Pro Gly Gly Leu Ser
        35                  40                  45

Ala Lys Ala Pro Ala Met Thr Pro Leu Met Leu Asp Thr Ser Ser Arg
    50                  55                  60

Lys Leu Val Ala Trp Asp Gly Thr Thr Asp Gly Ala Ala Val Gly Ile
65                  70                  75                  80

Leu Ala Val Ala Ala Asp Gln Thr Ser Thr Thr Leu Thr Phe Tyr Lys
                85                  90                  95

Ser Gly Thr Phe Arg Tyr Glu Asp Val Leu Trp Pro Glu Ala Ala Ser
            100                 105                 110

Asp Glu Thr Lys Lys Arg Thr Ala Phe Ala Gly Thr Ala Ile Ser Ile
        115                 120                 125
```

Val

<210> SEQ ID NO 12
<211> LENGTH: 1365
<212> TYPE: DNA
<213> ORGANISM: Artificial
<220> FEATURE:
<223> OTHER INFORMATION: Construct 6 Nucleotide Sequence

<400> SEQUENCE: 12

```
atggccgagg tgcagctggt ggagtctggg ggaagcctgg tcaagcctgg ggggtccctg      60
agactctcct gtgcagcctc tggattcacc ttcagtaact atagcatgaa ctgggtccgc     120
caggctccag ggaaggggct ggagtggatc tcatccatta gtggtagtag tagatacata     180
tactacgcag acttcgtgaa gggccgattc accatctcca gagacaacgc cacgaactca     240
ctgtacctgc aaatgaacag cctgagagcc gaggacacgg ctgtttatta ctgtgtgaga     300
tccagtatta cgattttttgg tggcggtatg gacgtctggg gcagaggcac cctggtcacc    360
gtctcctcag gtggaggcgg ttcaggcgga ggtggcagcg gcggtggcgg atcgcagtct    420
gtgctgactc agcctgcctc cgtgtctggg tctcctggac agtcgatcac catctcctgc    480
gctggaacca gcagtgacgt tggtggttat aactatgtct cctggtacca acaacaccca    540
ggcaaagccc ccaaactcat gatttatgag gacagtaagc ggccctcagg ggtttctaat    600
cgcttctctg gctccaagtc tggcaacacg gcctccctga caatctctgg gctccaggct    660
gaggacgagg ctgattatta ctgcagctca tatacaacca ggagcactcg agttttcggc    720
ggagggacca gctggccgt cctaggtgcg gccgcagaat tcggcagcgg ttctggccgg    780
ctgaacttcg ggacgacat ccccagcgct cttcgaatcg gaagaagaa gcgctggaac      840
agcattgagg agcggcgcat ccaccaggag agcgagctgc actcctacct ctccaggctc    900
attgccgcgg agcgtgagag ggagctggaa gagtgccagc gaaaccacga gggtgatgag    960
gacgacagcc acgtccgggc ccagcaggcc tgcattgagg ccaagcacga caagtacatg   1020
gcggacatgg acgagctttt ttctcaggtg gatgagaaga ggaagaagcg agacatcccc   1080
gactacctgt gtggcaagat cagctttgag ctgatgcggg agccgtgcat cacgcccagt   1140
ggcatcacct acgaccgcaa ggacatcgag gagcacctgc agcgtgtggg tcatttttgac  1200
cccgtgaccc ggagccccct gacccaggaa cagctcatcc ccaacttggc tatgaaggag   1260
gttattgacg cattcatctc tgagaatggc tgggtggagg attacgtcga cggagcagac   1320
tacaaggacg atgacgacaa gggacatcat catcatcatc actaa                   1365
```

<210> SEQ ID NO 13
<211> LENGTH: 454
<212> TYPE: PRT
<213> ORGANISM: Artificial
<220> FEATURE:
<223> OTHER INFORMATION: Construct 6 Amino Acid Sequence

<400> SEQUENCE: 13

```
Met Ala Glu Val Gln Leu Val Glu Ser Gly Gly Ser Leu Val Lys Pro
1               5                   10                  15
Gly Gly Ser Leu Arg Leu Ser Cys Ala Ala Ser Gly Phe Thr Phe Ser
            20                  25                  30
Asn Tyr Ser Met Asn Trp Val Arg Gln Ala Pro Gly Lys Gly Leu Glu
        35                  40                  45
Trp Ile Ser Ser Ile Ser Gly Ser Ser Arg Tyr Ile Tyr Tyr Ala Asp
    50                  55                  60
```

Phe Val Lys Gly Arg Phe Thr Ile Ser Arg Asp Asn Ala Thr Asn Ser
65                  70                  75                  80

Leu Tyr Leu Gln Met Asn Ser Leu Arg Ala Glu Asp Thr Ala Val Tyr
            85                  90                  95

Tyr Cys Val Arg Ser Ser Ile Thr Ile Phe Gly Gly Gly Met Asp Val
                100                 105                 110

Trp Gly Arg Gly Thr Leu Val Thr Val Ser Ser Gly Gly Gly Gly Ser
            115                 120                 125

Gly Gly Gly Gly Ser Gly Gly Gly Ser Gln Ser Val Leu Thr Gln
130                 135                 140

Pro Ala Ser Val Ser Gly Ser Pro Gly Gln Ser Ile Thr Ile Ser Cys
145                 150                 155                 160

Ala Gly Thr Ser Ser Asp Val Gly Gly Tyr Asn Tyr Val Ser Trp Tyr
                165                 170                 175

Gln Gln His Pro Gly Lys Ala Pro Lys Leu Met Ile Tyr Glu Asp Ser
            180                 185                 190

Lys Arg Pro Ser Gly Val Ser Asn Arg Phe Ser Gly Ser Lys Ser Gly
            195                 200                 205

Asn Thr Ala Ser Leu Thr Ile Ser Gly Leu Gln Ala Glu Asp Glu Ala
210                 215                 220

Asp Tyr Tyr Cys Ser Ser Tyr Thr Thr Arg Ser Thr Arg Val Phe Gly
225                 230                 235                 240

Gly Gly Thr Lys Leu Ala Val Leu Gly Ala Ala Ala Glu Phe Gly Ser
                245                 250                 255

Gly Ser Gly Arg Leu Asn Phe Gly Asp Asp Ile Pro Ser Ala Leu Arg
            260                 265                 270

Ile Ala Lys Lys Lys Arg Trp Asn Ser Ile Glu Glu Arg Arg Ile His
            275                 280                 285

Gln Glu Ser Glu Leu His Ser Tyr Leu Ser Arg Leu Ile Ala Ala Glu
290                 295                 300

Arg Glu Arg Glu Leu Glu Glu Cys Gln Arg Asn His Glu Gly Asp Glu
305                 310                 315                 320

Asp Asp Ser His Val Arg Ala Gln Gln Ala Cys Ile Glu Ala Lys His
                325                 330                 335

Asp Lys Tyr Met Ala Asp Met Asp Glu Leu Phe Ser Gln Val Asp Glu
            340                 345                 350

Lys Arg Lys Lys Arg Asp Ile Pro Asp Tyr Leu Cys Gly Lys Ile Ser
            355                 360                 365

Phe Glu Leu Met Arg Glu Pro Cys Ile Thr Pro Ser Gly Ile Thr Tyr
370                 375                 380

Asp Arg Lys Asp Ile Glu Glu His Leu Gln Arg Val Gly His Phe Asp
385                 390                 395                 400

Pro Val Thr Arg Ser Pro Leu Thr Gln Glu Gln Leu Ile Pro Asn Leu
                405                 410                 415

Ala Met Lys Glu Val Ile Asp Ala Phe Ile Ser Glu Asn Gly Trp Val
            420                 425                 430

Glu Asp Tyr Val Asp Gly Ala Asp Tyr Lys Asp Asp Asp Lys Gly
            435                 440                 445

His His His His His
    450

<210> SEQ ID NO 14
<211> LENGTH: 1362

```
<212> TYPE: DNA
<213> ORGANISM: Artificial
<220> FEATURE:
<223> OTHER INFORMATION: Construct 7 Nucleotide Sequence

<400> SEQUENCE: 14
atggcccttg aagtgcaatt ggtggaaagc ggcggcggcc tggtgcaacc gggcggcagc      60
ctgcgtctga gctgcgcggc ctccggattt acctttagca gctatgcgat gagctgggtg     120
cgccaagccc ctgggaaggg tctcgagtgg gtgagcgcga ttagcggtag cggcggcagc     180
acctattatg cggatagcgt gaaaggccgt tttaccattt cacgtgataa ttcgaaaaac     240
accctgtatc tgcaaatgaa cagcctgcgt gcggaagata cggccgtgta ttattgcgcg     300 cgttttttctt atgtttctgg tatggattat tggggccaag caccctggt gacggttagc      360 tcagcgggtg gcggttctgg cggcggtggg agcggtggcg gtggttctgg cggtggtggt     420
tccgatatcg aactgaccca gccgccttca gtgagcgttg caccaggtca gaccgcgcgt     480
atctcgtgta gcggcgatgc gctggcgat aaatacgcga gctggtacca gcagaaaccc      540
gggcaggcgc cagttctggt gatttatgat gattctgacc gtccctcagg catcccggaa     600
cgctttagcg gatccaacag cggcaacacc gcgaccctga ccattagcgg cactcaggcg     660
gaagacgaag cggattatta ttgccagagc tatgacaatg ttttttatgg tactgtgttt     720
ggcggcggca cgaagttaac cgttcttggc caggaattcg gcagcggttc tggccggctg     780
aacttcgggg acgacatccc cagcgctctt cgaatcgcga agaagaagcg ctggaacagc     840
attgaggagc ggcgcatcca ccaggagagc gagctgcact cctacctctc caggctcatt     900
gccgcggagc gtgagaggga gctggaagag tgccagcgaa ccacgagggg tgatgaggac     960
gacagccacg tccgggccca gcaggcctgc attgaggcca gcacgacaa gtacatggcg     1020 gacatggacg agcttttttc tcaggtggat gagaagagga gaagcgaga catccccgac     1080 tacctgtgtg caagatcag ctttgagctg atgcgggagc cgtgcatcac gcccagtggc     1140
atcacctacg accgcaagga catcgaggag cacctgcagc gtgtgggtca ttttgacccc     1200
gtgacccgga ccccctgac ccaggaacag ctcatcccca acttggctat gaaggaggtt     1260
attgacgcat tcatctctga aatggctgg gtggaggatt acgtcgacgg agcagactac     1320
aaggacgatg acgacaaggg acatcatcat catcatcact aa                        1362

<210> SEQ ID NO 15
<211> LENGTH: 453
<212> TYPE: PRT
<213> ORGANISM: Artificial
<220> FEATURE:
<223> OTHER INFORMATION: Construct 7 Amino Acid Sequence

<400> SEQUENCE: 15

Met Ala Leu Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
```

```
                        85                  90                  95
Tyr Tyr Cys Ala Arg Phe Ser Tyr Val Ser Gly Met Asp Tyr Trp Gly
            100                 105                 110

Gln Gly Thr Leu Val Thr Val Ser Ala Gly Gly Gly Ser Gly Gly
            115                 120                 125

Gly Gly Ser Gly Gly Gly Ser Gly Gly Gly Ser Asp Ile Glu
            130                 135                 140

Leu Thr Gln Pro Pro Ser Val Ser Val Ala Pro Gly Gln Thr Ala Arg
145                 150                 155                 160

Ile Ser Cys Ser Gly Asp Ala Leu Gly Asp Lys Tyr Ala Ser Trp Tyr
            165                 170                 175

Gln Gln Lys Pro Gly Gln Ala Pro Val Leu Val Ile Tyr Asp Asp Ser
            180                 185                 190

Asp Arg Pro Ser Gly Ile Pro Glu Arg Phe Ser Gly Ser Asn Ser Gly
            195                 200                 205

Asn Thr Ala Thr Leu Thr Ile Ser Gly Thr Gln Ala Glu Asp Glu Ala
            210                 215                 220

Asp Tyr Tyr Cys Gln Ser Tyr Asp Asn Asp Phe Tyr Gly Thr Val Phe
225                 230                 235                 240

Gly Gly Gly Thr Lys Leu Thr Val Leu Gly Gln Glu Phe Gly Ser Gly
            245                 250                 255

Ser Gly Arg Leu Asn Phe Gly Asp Asp Ile Pro Ser Ala Leu Arg Ile
            260                 265                 270

Ala Lys Lys Lys Arg Trp Asn Ser Ile Glu Glu Arg Ile His Gln
            275                 280                 285

Glu Ser Glu Leu His Ser Tyr Leu Ser Arg Leu Ile Ala Ala Glu Arg
            290                 295                 300

Glu Arg Glu Leu Glu Cys Gln Arg Asn His Glu Gly Asp Glu Asp
305                 310                 315                 320

Asp Ser His Val Arg Ala Gln Gln Ala Cys Ile Glu Ala Lys His Asp
            325                 330                 335

Lys Tyr Met Ala Asp Met Asp Glu Leu Phe Ser Gln Val Asp Glu Lys
            340                 345                 350

Arg Lys Lys Arg Asp Ile Pro Asp Tyr Leu Cys Gly Lys Ile Ser Phe
            355                 360                 365

Glu Leu Met Arg Glu Pro Cys Ile Thr Pro Ser Gly Ile Thr Tyr Asp
            370                 375                 380

Arg Lys Asp Ile Glu Glu His Leu Gln Arg Val Gly His Phe Asp Pro
385                 390                 395                 400

Val Thr Arg Ser Pro Leu Thr Gln Glu Gln Leu Ile Pro Asn Leu Ala
            405                 410                 415

Met Lys Glu Val Ile Asp Ala Phe Ile Ser Glu Asn Gly Trp Val Glu
            420                 425                 430

Asp Tyr Val Asp Gly Ala Asp Tyr Lys Asp Asp Asp Lys Gly His
            435                 440                 445

His His His His His
    450

<210> SEQ ID NO 16
<211> LENGTH: 369
<212> TYPE: DNA
<213> ORGANISM: Artificial
<220> FEATURE:
<223> OTHER INFORMATION: Construct 8 Nucleotide Sequence
```

```
<400> SEQUENCE: 16
atgtacccgt acgacgttcc ggactacgct catatgcttg cgagcaaaga aacctttacc      60
cattaccagc cgcagggcaa cagtgacccg gctcataccg caaccgcgcc cggcggattg     120
agtgcgaaag cgcctgcaat gaccccgctg atgctggaca cctccagccg taagctggtt     180
gcgtgggatg gcaccaccga cggtgctgcc gttggcattc ttgcggttgc tgctgaccag     240
accagcacca cgctgacgtt ctacaagtcc ggcacgttcc gttatgagga tgtgctctgg     300
ccggaggctg ccagcgacga gacgaaaaaa cggaccgcgt ttgccggaac ggcaatcagc     360
atcgtttaa                                                              369

<210> SEQ ID NO 17
<211> LENGTH: 122
<212> TYPE: PRT
<213> ORGANISM: Artificial
<220> FEATURE:
<223> OTHER INFORMATION: Construct 8 Amino Acid Sequence

<400> SEQUENCE: 17

Met Tyr Pro Tyr Asp Val Pro Asp Tyr Ala His Met Leu Ala Ser Lys
1               5                   10                  15

Glu Thr Phe Thr His Tyr Gln Pro Gln Gly Asn Ser Asp Pro Ala His
            20                  25                  30

Thr Ala Thr Ala Pro Gly Gly Leu Ser Ala Lys Ala Pro Ala Met Thr
        35                  40                  45

Pro Leu Met Leu Asp Thr Ser Ser Arg Lys Leu Val Ala Trp Asp Gly
    50                  55                  60

Thr Thr Asp Gly Ala Ala Val Gly Ile Leu Ala Val Ala Ala Asp Gln
65                  70                  75                  80

Thr Ser Thr Thr Leu Thr Phe Tyr Lys Ser Gly Thr Phe Arg Tyr Glu
                85                  90                  95

Asp Val Leu Trp Pro Glu Ala Ala Ser Asp Glu Thr Lys Lys Arg Thr
                100                 105                 110

Ala Phe Ala Gly Thr Ala Ile Ser Ile Val
            115                 120
```